US009547380B2

(12) United States Patent
Parazynski

(10) Patent No.: US 9,547,380 B2
(45) Date of Patent: Jan. 17, 2017

(54) MULTI-DEGREES-OF-FREEDOM HAND CONTROLLER

(71) Applicant: Fluidity Technologies, Inc., Houston, TX (US)

(72) Inventor: Scott Edward Parazynski, Houston, TX (US)

(73) Assignee: Fluidity Technologies, Inc., Houston, TX (US)

( * ) Notice: Subject to any disclaimer, the term of this patent is extended or adjusted under 35 U.S.C. 154(b) by 0 days.

(21) Appl. No.: 15/071,624

(22) Filed: Mar. 16, 2016

(65) Prior Publication Data

US 2016/0195939 A1 Jul. 7, 2016

Related U.S. Application Data

(63) Continuation of application No. 13/797,184, filed on Mar. 12, 2013.

(Continued)

(51) Int. Cl.
*G06F 3/0346* (2013.01)
*G08C 19/16* (2006.01)
(Continued)

(52) U.S. Cl.
CPC ............. *G06F 3/0346* (2013.01); *A61B 34/30* (2016.02); *A61B 34/37* (2016.02); *A61B 34/74* (2016.02);
(Continued)

(58) Field of Classification Search
CPC ....... G06F 3/0346; G06F 3/0338; A61B 34/74
See application file for complete search history.

(56) References Cited

U.S. PATENT DOCUMENTS 3,260,826 A 7/1966 Johnson
4,012,014 A * 3/1977 Marshall ................. B64C 13/04
244/234

(Continued)

OTHER PUBLICATIONS

Pamplona et al., "The image-based data glove," Proceedings of the 10th Symposium on Virtual and Augmented Reality. João Pessoa, Brazil. pp. 204-211. 2008.

(Continued)

*Primary Examiner* — Joseph Feild
*Assistant Examiner* — Rufus Point
(74) *Attorney, Agent, or Firm* — Davis Wright Tremaine LLP

(57) ABSTRACT

Disclosed is a controller including a first control member, a second control member that extends from a portion of the first control member, and a controller processor that is operable to produce a rotational movement output signal in response to movement of the first control member, and a translational movement output signal in response to movement of the second control member relative to the first control member. The rotational movement output signal may be any of a pitch movement output signal, a yaw movement output signal, and a roll movement output signal, and the translational movement output signal may be any of an x-axis movement output signal, a y-axis movement output signal, and a z-axis movement output signal. In exemplary embodiments, the first control member may be gripped and moved using a single hand, and the second control member may be moved using one or more digits of the single hand, thus permitting highly intuitive, single-handed control of multiple degrees of freedom, to and including, all six degrees of rotational and translational freedom without any inadvertent cross-coupling inputs.

27 Claims, 24 Drawing Sheets

Related U.S. Application Data

(60) Provisional application No. 61/642,118, filed on May 3, 2012.

(51) Int. Cl.
    *G06F 3/0338*     (2013.01)
    *A61B 5/00*     (2006.01)

(52) U.S. Cl.
    CPC .............. *G06F 3/0338* (2013.01); *G08C 19/16* (2013.01); *A61B 5/7475* (2013.01); *A61B 2560/0487* (2013.01); *G05B 2219/45123* (2013.01)

(56) References Cited

U.S. PATENT DOCUMENTS

| | | | | |
|---|---|---|---|---|
| 4,216,467 | A * | 8/1980 | Colston | B25J 13/02 341/176 |
| 4,420,808 | A * | 12/1983 | Diamond | B60N 2/4693 244/177 |
| 4,584,510 | A * | 4/1986 | Hollow | B64C 13/04 244/234 |
| 5,042,314 | A * | 8/1991 | Rytter | B62D 1/12 180/333 |
| 5,128,671 | A * | 7/1992 | Thomas, Jr. | A63F 13/06 244/191 |
| 5,223,776 | A * | 6/1993 | Radke | B25J 13/02 200/5 R |
| 5,459,382 | A | 10/1995 | Jacobus et al. | |
| 5,565,891 | A * | 10/1996 | Armstrong | G05G 9/04737 345/156 |
| D375,765 | S * | 11/1996 | Kawasaki | D14/413 |
| D389,198 | S * | 1/1998 | Hama | D14/413 |
| 5,749,577 | A * | 5/1998 | Couch | A63F 13/06 273/148 B |
| 5,781,180 | A * | 7/1998 | Couch | A63F 13/06 273/148 B |
| 5,831,408 | A | 11/1998 | Jacobus et al. | |
| 5,963,196 | A * | 10/1999 | Nishiumi | A63F 13/02 345/161 |
| H1822 | H * | 12/1999 | Kelley | E02F 9/2004 180/333 |
| 6,222,525 | B1 * | 4/2001 | Armstrong | G06F 3/0213 345/161 |
| 6,429,849 | B1 * | 8/2002 | An | G05G 9/047 345/161 |
| 6,597,347 | B1 * | 7/2003 | Yasutake | G06F 3/0338 178/18.01 |
| 6,624,806 | B2 * | 9/2003 | Hsu | G05G 9/04788 273/148 B |
| 6,865,342 | B2 * | 3/2005 | Hirata | G05G 9/047 348/211.7 |
| 7,131,389 | B1 * | 11/2006 | Hawkes | B63G 8/001 114/320 |
| 7,170,420 | B2 * | 1/2007 | Phifer | G08C 23/04 340/12.55 |
| 7,575,491 | B1 * | 8/2009 | Martin | B63H 21/213 440/6 |
| 7,793,890 | B2 * | 9/2010 | Scherer | A63H 30/04 244/189 |
| 7,823,685 | B2 * | 11/2010 | Blind | A01B 63/00 180/315 |
| 7,931,239 | B2 * | 4/2011 | Pedersen | B60V 1/06 244/189 |
| 8,089,225 | B2 * | 1/2012 | Goossen | G05D 1/0016 318/16 |
| 8,100,218 | B2 * | 1/2012 | Case | B62D 1/12 180/315 |
| 8,258,917 | B2 * | 9/2012 | Cai | G06F 3/0346 180/167 |
| 8,300,012 | B2 * | 10/2012 | Yamamoto | G06F 3/0346 345/158 |
| 8,344,914 | B2 * | 1/2013 | Yeh | G05G 9/047 341/20 |
| 8,380,402 | B2 * | 2/2013 | Hobenshield | G05G 9/04785 172/50 |
| D678,281 | S * | 3/2013 | Yung | D14/401 |
| 8,576,168 | B2 * | 11/2013 | Kabasawa | G06F 3/0346 345/157 |
| 8,716,973 | B1 * | 5/2014 | Lammertse | G06F 3/016 318/560 |
| 8,866,597 | B2 * | 10/2014 | Brendel | G08C 17/02 340/12.5 |
| 2003/0006956 | A1 * | 1/2003 | Wu | G06K 9/22 345/156 |
| 2003/0214484 | A1 * | 11/2003 | Haywood | G06F 3/0338 345/163 |
| 2005/0104742 | A1 * | 5/2005 | Phifer | G08C 23/04 340/12.55 |
| 2005/0277470 | A1 * | 12/2005 | Watanachote | A63F 13/06 463/37 |
| 2006/0164383 | A1 * | 7/2006 | Machin | G05G 9/047 345/156 |
| 2006/0262000 | A1 * | 11/2006 | Strong | G08C 17/00 341/176 |
| 2007/0080934 | A1 * | 4/2007 | Chen | G06F 3/0383 345/156 |
| 2008/0063400 | A1 * | 3/2008 | Hudson | A63H 30/04 398/106 |
| 2008/0132334 | A1 * | 6/2008 | Nonaka | A63F 13/10 463/37 |
| 2008/0174550 | A1 * | 7/2008 | Laurila | A63F 13/02 345/158 |
| 2009/0179869 | A1 * | 7/2009 | Slotznick | G06F 3/0202 345/173 |
| 2010/0097309 | A1 * | 4/2010 | Nishida | G06F 3/0346 345/156 |
| 2010/0302017 | A1 * | 12/2010 | Guglielmo | G05G 9/047 340/407.2 |
| 2011/0148667 | A1 * | 6/2011 | Yeh | G05G 9/047 341/20 |
| 2011/0213384 | A1 * | 9/2011 | Jeong | A61B 19/2203 606/130 |
| 2011/0219899 | A1 | 9/2011 | Dize et al. | |
| 2012/0187238 | A1 * | 7/2012 | Lam | A63H 27/12 244/17.21 |
| 2013/0147611 | A1 * | 6/2013 | Brendel | G08C 17/02 340/12.5 |

OTHER PUBLICATIONS

Wilbert et al., "Semi-robotic 6 degee of freedom positioning for intracranial high precision radiotherapy; first phantom and clinical results," Radiation Oncology, 5(42). 11 Pages. May 26, 2010.

Zhai, "Human performance in six degree of freedom input control," Doctoral Dissertation University of Toronto; Graduate Department of Industrial Engineering. 179 Pages. 1995.

* cited by examiner

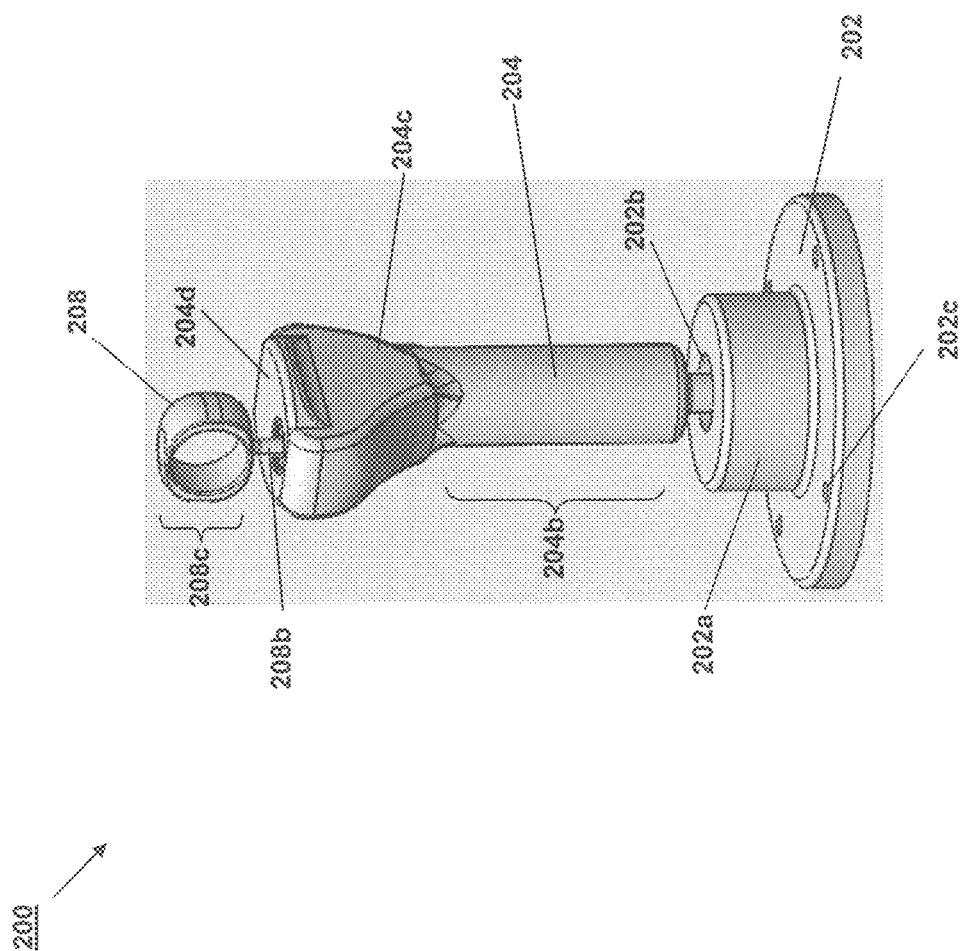

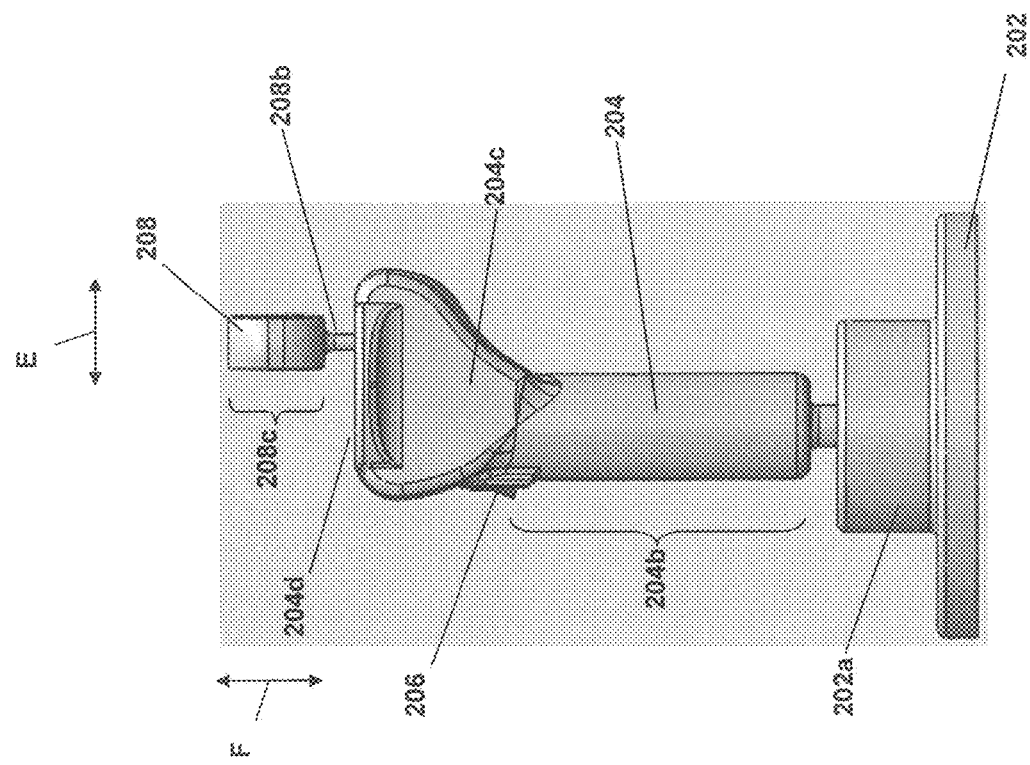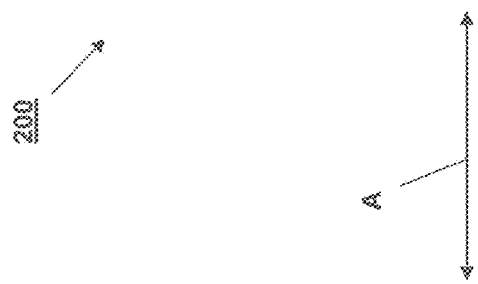

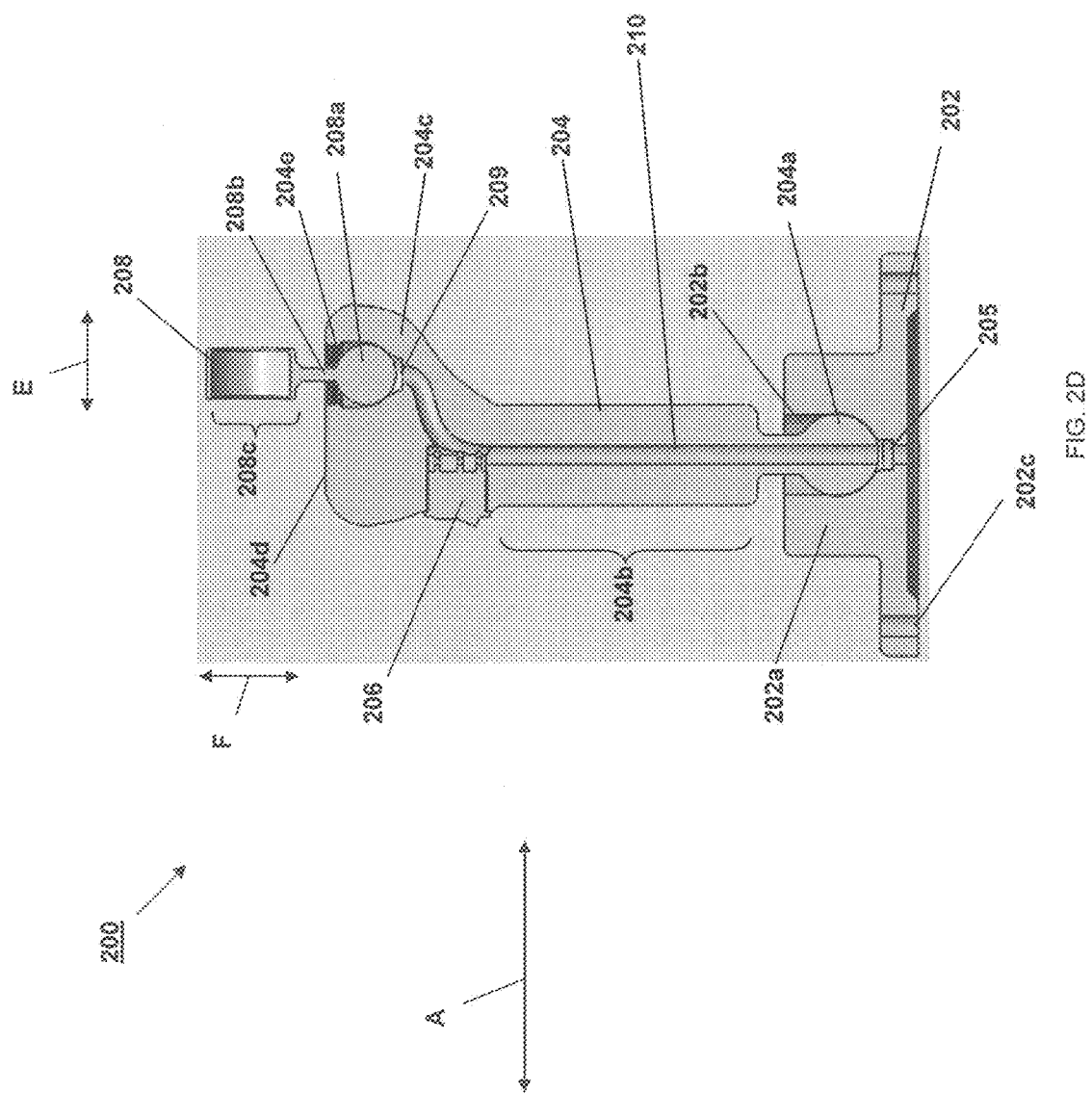

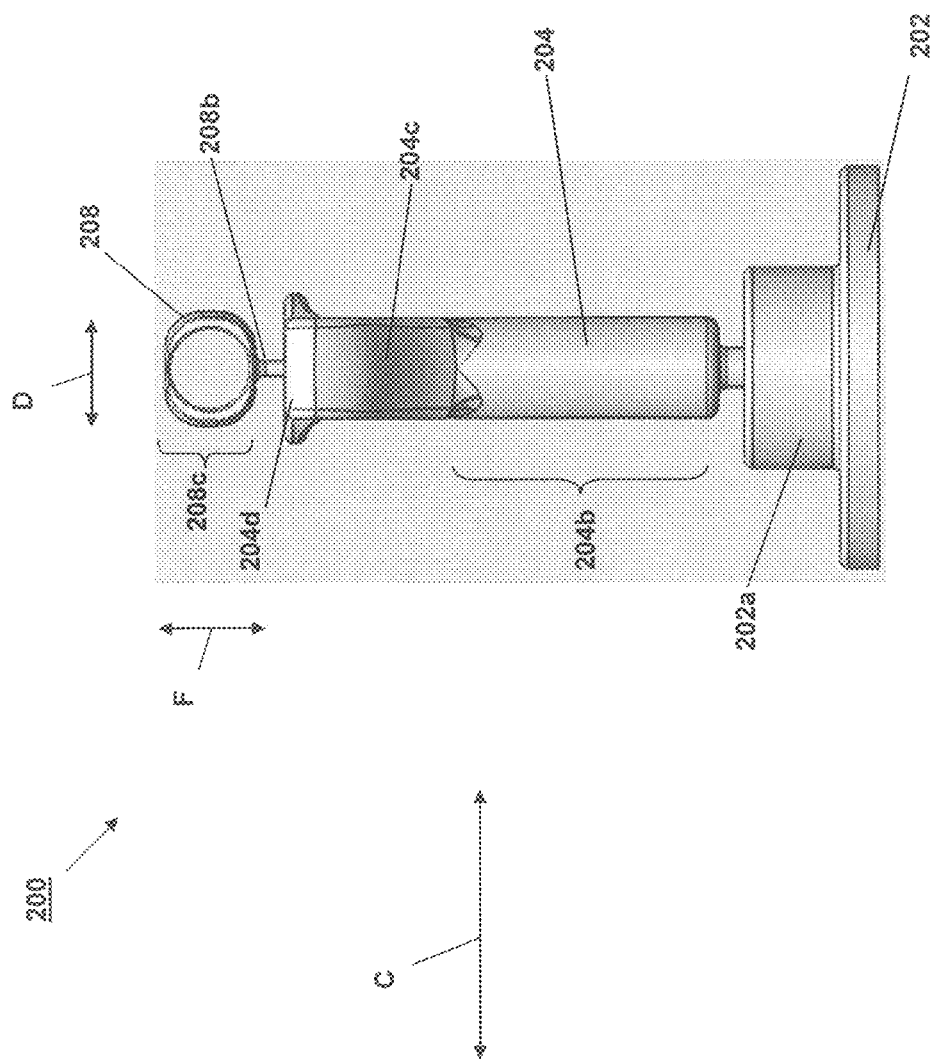

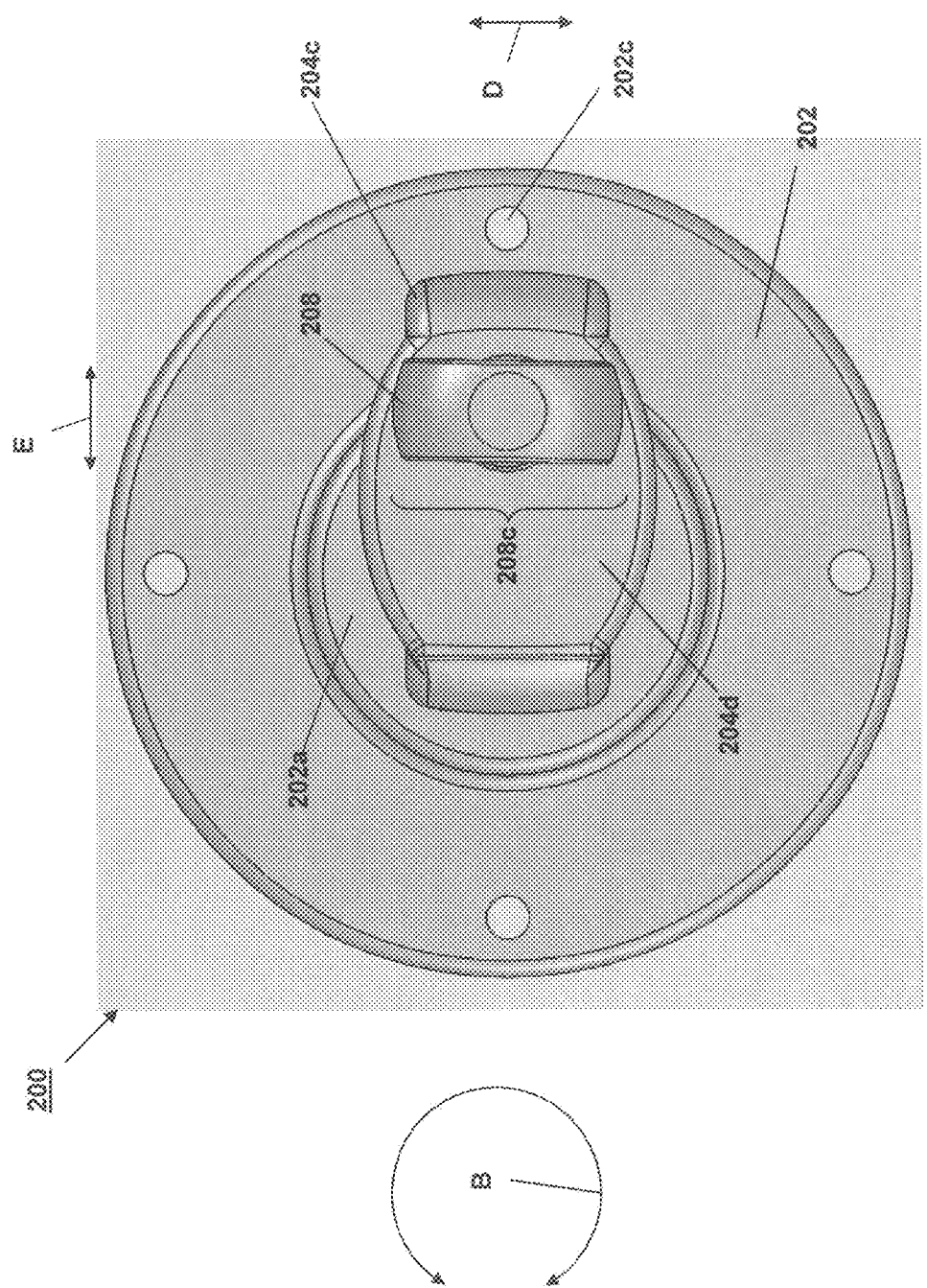

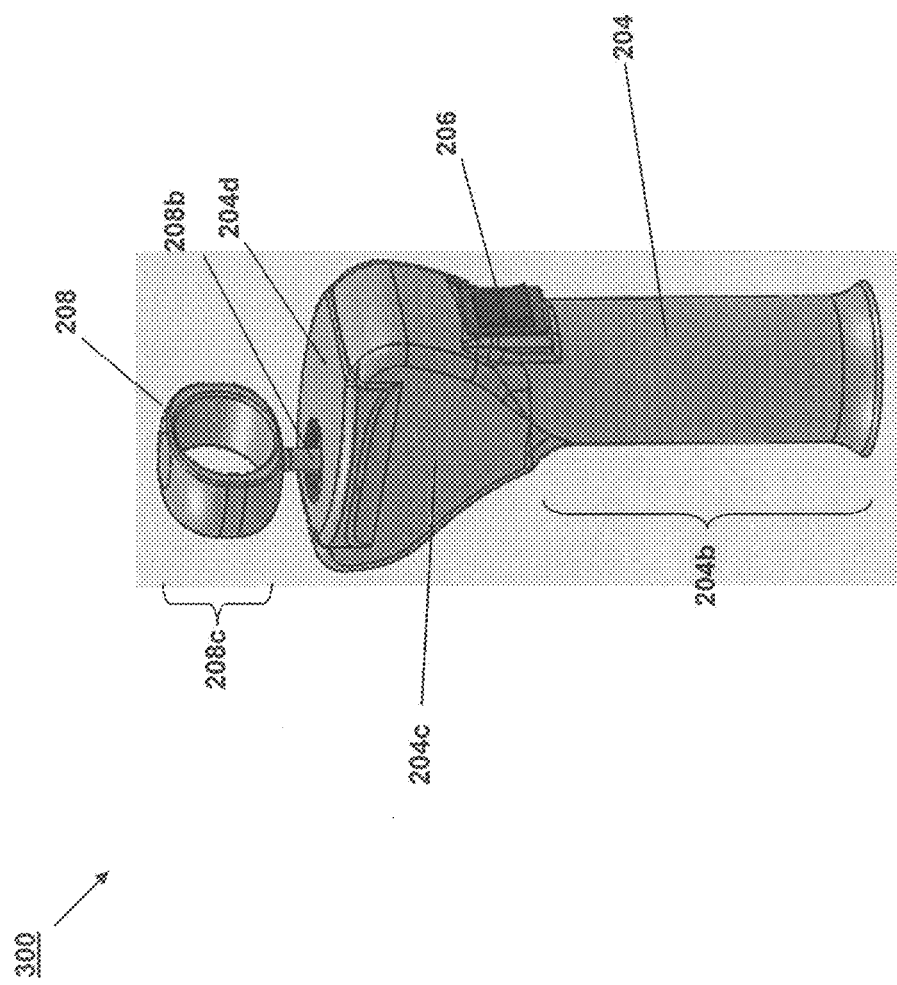

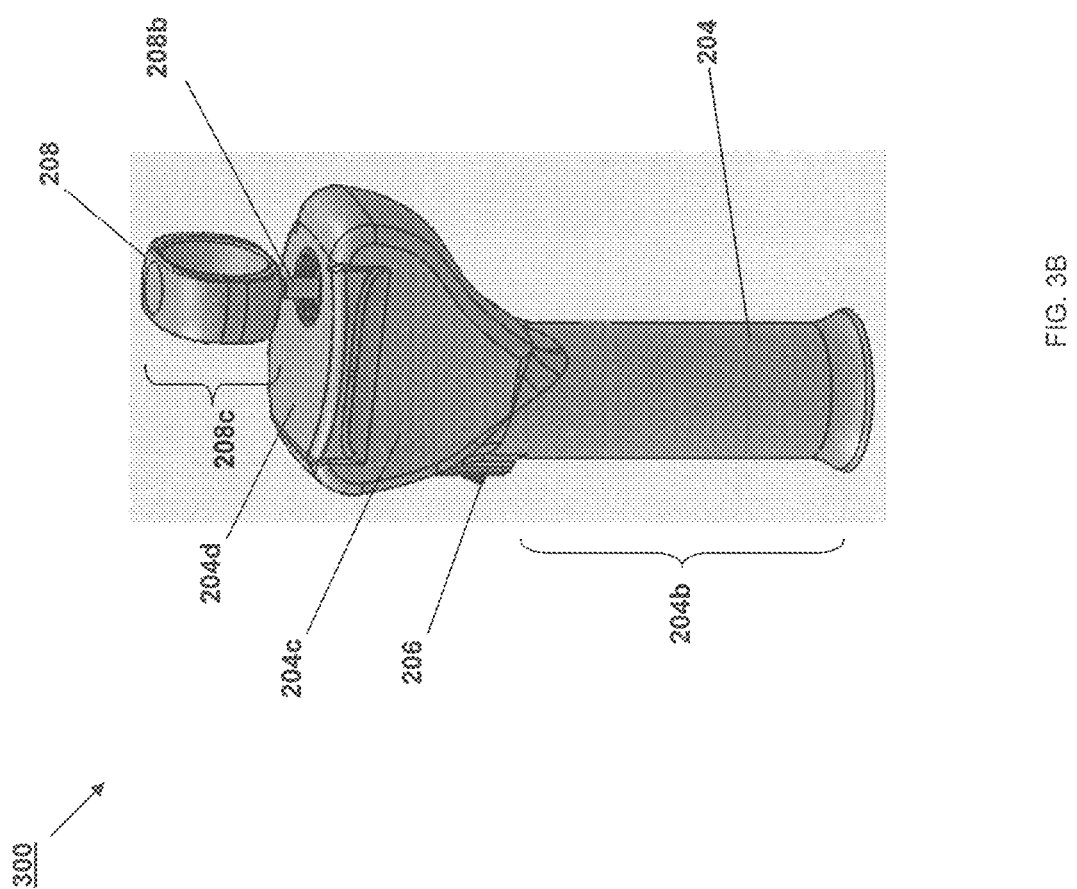

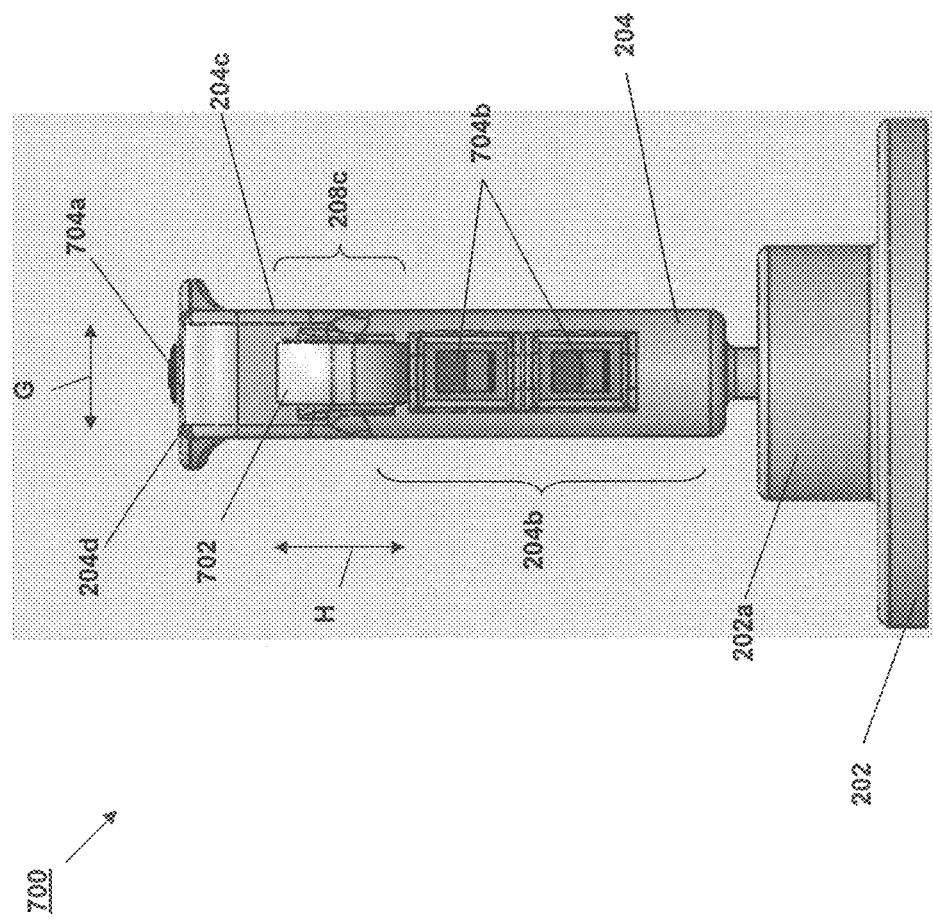

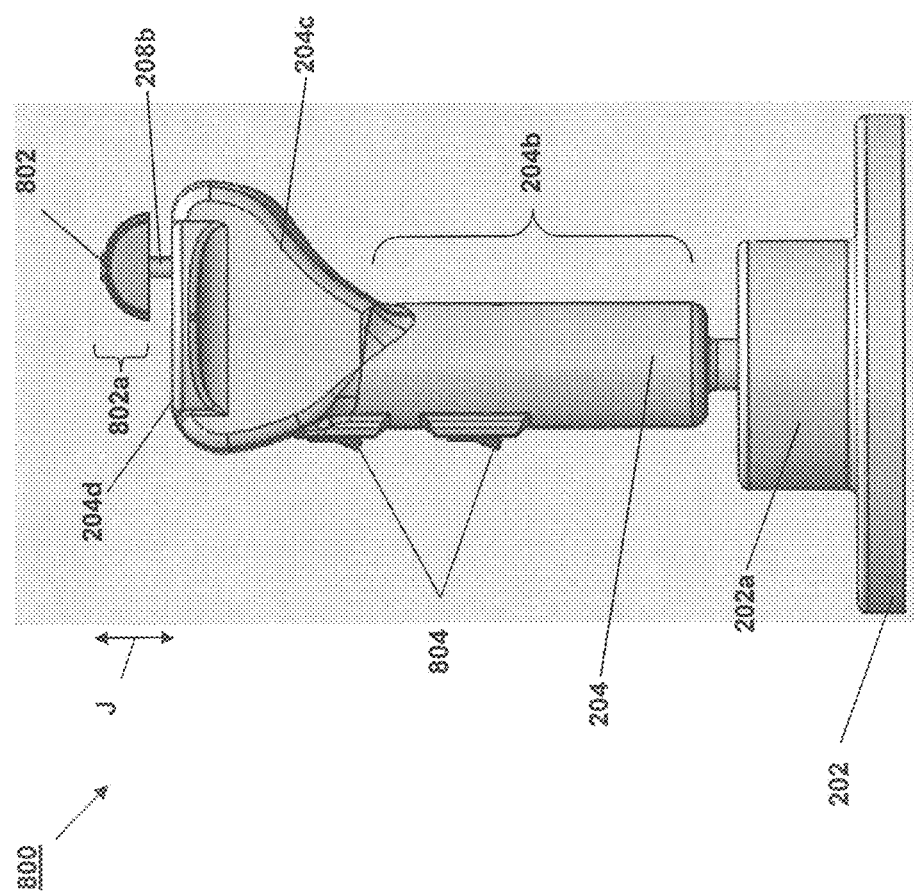

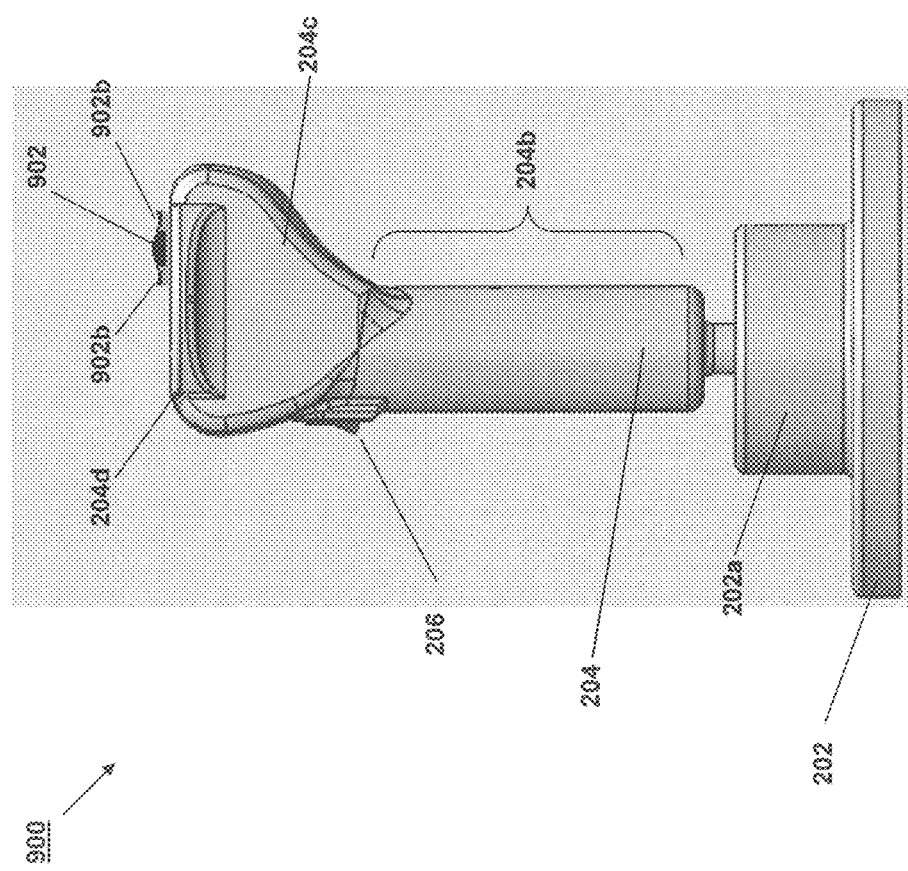

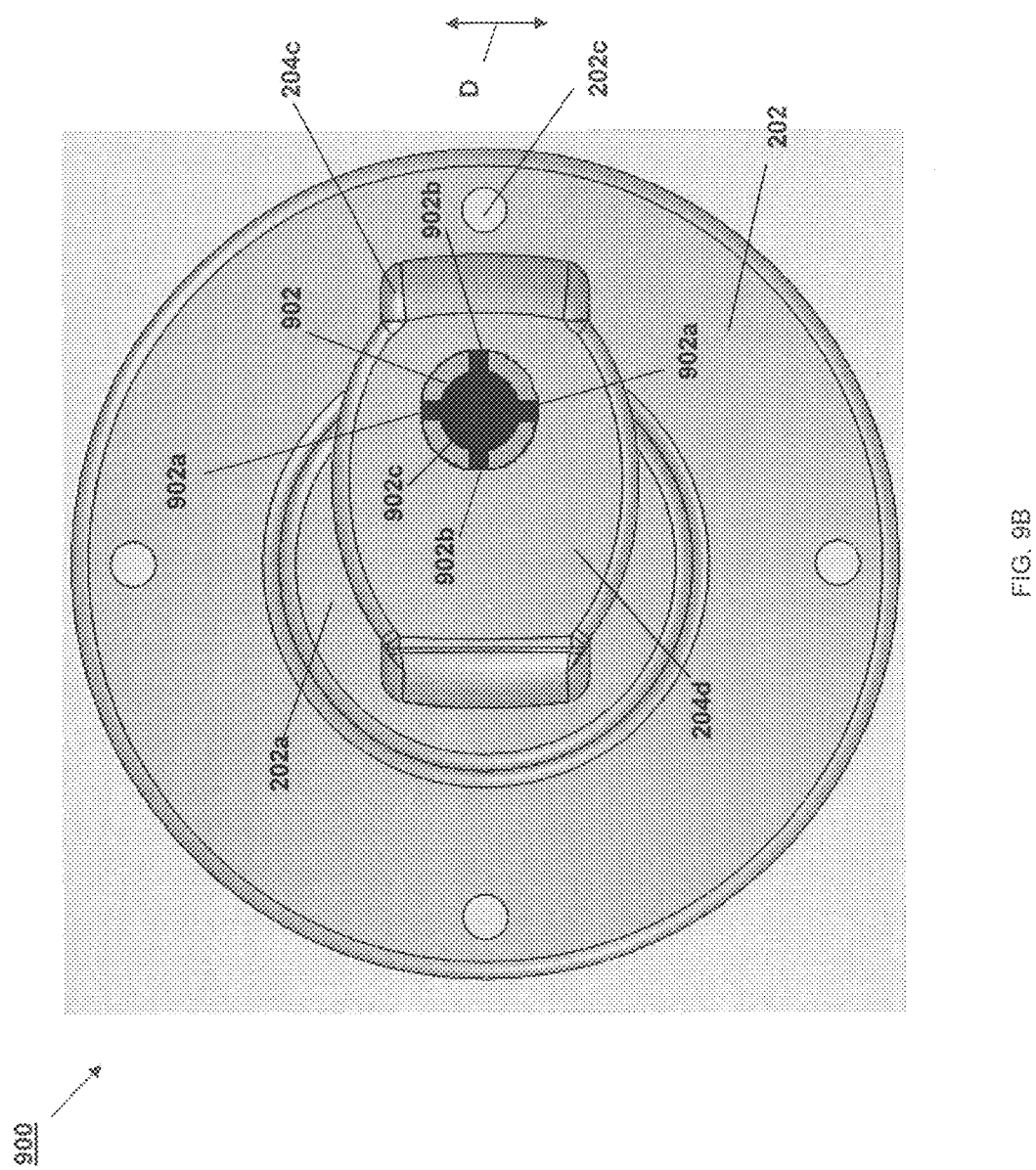

MULTI-DEGREES-OF-FREEDOM HAND CONTROLLER

The present application is a continuation of U.S. patent application Ser. No. 13/797,184 filed Mar. 12, 2013, which claims priority to U.S. Provisional Patent Application No. 61/642,118 filed on May 3, 2012, the entire contents of which is specifically incorporated herein by express reference thereto.

BACKGROUND OF THE INVENTION

Field of the Invention

The present disclosure relates generally to control systems and more particularly to a controller that provides a user with the ability to send navigation signals for up to six independent degrees of freedom, without cross-coupling, using a controller that is operable with a single hand. In some embodiments, the controller is operable to decouple translational motion from attitude adjustment.

BRIEF SUMMARY OF THE INVENTION

A controller includes (a) a first control member, (b) a second control member extending from a portion of the first control member, and (c) a controller processor coupled to the first control member and the second control member, wherein the controller processor is operable to produce a rotational movement output signal in response to movement of the first control member, wherein the controller processor is operable to produce a translational movement output signal in response to movement of the second control member relative to the first control member. In an embodiment, the controller processor is operable to produce one or more of a pitch movement output signal in response to a first predetermined movement of the first control member, a yaw movement output signal in response to a second predetermined movement of the first control member, and a roll movement output signal in response to a third predetermined movement of the first control member. In an embodiment, the controller processor is operable to produce one or more of an x-axis movement output signal in response to a first predetermined movement of the second control member, a y-axis movement output signal in response to a second predetermined movement of the second control member, and a z-axis movement output signal in response to a third predetermined movement of the second control member. In an embodiment, the controller processor is operable to produce at least two different types of rotational movement output signals in response to movement of the first control member, and wherein the controller processor is operable to produce at least two different types of translational movement output signals in response to movement of the second control member relative to the first control member. Furthermore, in some embodiments, the controller processor is operable to produce output signals for movement in one degree of freedom to six degrees of freedom simultaneously (e.g., three rotational movement output signals and three translational movement output signals). In an embodiment, the controller processor is operable to produce at least three different types of rotational movement output signals in response to movement of the first control member, and wherein the controller processor is operable to produce at least three different types of translational movement output signals in response to movement of the second control member relative to the first control member. In an embodiment, the first control member is configured to be gripped and moved using a single hand, and wherein the second control member is configured to be moved using one or more digits on the single hand. In an embodiment, the one or more digits include the thumb. In an embodiment, the first control member is moveably coupled to a base, and wherein the controller processor is operable to produce the rotational movement output signal in response to movement of the first control member relative to the base. In an embodiment, the first control member comprises at least one motion sensor, and wherein the controller processor is operable to produce the rotational movement output signal in response to movement of the first control member in space that is detected by the at least one motion sensor. In an embodiment, a control button is located on the first control member. Furthermore, multi-function switches, trim control, and/or other functional switches and controls may be added to either of the first control member and/or the second control member.

A computer system includes (a) a processor, (b) a non-transitory, computer-readable medium coupled to the processor and including instruction that, when executed by the processor, cause the processor to provide a control program, and (c) a user input device coupled to the processor, the user input device comprising: (i) a first control member, wherein movement of the first control member causes the processor to provide one of a plurality of rotational movement instructions in the control program, and (ii) a second control member extending from a portion of the first control member, wherein movement of the second control member causes the processor to provide one of a plurality of translational movement instructions in the control program. In an embodiment, a first predetermined movement of the first control member causes the processor to provide a pitch movement instruction in the control program, a second predetermined movement of the first control member causes the processor to provide a yaw movement instruction in the control program, and a third predetermined movement of the first control member cause the processor to provide a roll movement instruction in the control program. In an embodiment, a first predetermined movement of the second control member causes the processor to provide an x-axis movement instruction in the control program, a second predetermined movement of the second control member causes the processor to provide a y-axis movement instruction in the control program, and a third predetermined movement of the second control member causes the processor to provide a z-axis movement instruction in the control program. In an embodiment, the first control member is configured to be gripped and moved using a single hand, and wherein the second control member is configured to be moved using one or more digits on the single hand. In an embodiment, the one or more digits includes the thumb. In an embodiment, the first control member is moveably coupled to a base, and wherein movement of the first control member relative to the base causes the processor to provide the one of a plurality of rotational movement instructions in the control program. In an embodiment, the first control member comprises at least one motion sensor, and wherein movement of the first control member in space that is detected by the at least one motion sensor causes the processor to provide the one of a plurality of translational movement instructions in the control program.

A control method includes: (a) providing a controller including a first control member and a second control member extending from a portion of the first control member, (b) sending a rotational movement output signal in response to moving the first control member, and (c) sending a translational movement output signal in response to moving the second control member relative to the first control member. In an embodiment, the sending the rotational movement output signal in response to moving the first control member includes sending a pitch movement output signal in response to a first predetermined movement of the first control member, sending a yaw movement output signal in response to a second predetermined movement of the first control member, and sending a roll movement output signal in response to a third predetermined movement of the first control member. In an embodiment, the sending the translational movement output signal in response to moving the second control member relative to the first control member includes sending an x-axis movement output signal in response to a first predetermined movement of the second control member, sending a y-axis movement output signal in response to a second predetermined movement of the second control member, and sending a z-axis movement output signal in response to a third predetermined movement of the second control member. In an embodiment, the moving the first control member includes gripping and moving the first control member using a single hand, and wherein the moving the second control member relative to the first control member includes moving the second control member using a thumb on the single hand. In an embodiment, the sending the rotational movement output signal in response to moving the first control member includes detecting the movement of the first control member about a moveable coupling on a base. In an embodiment, the sending the rotational movement output signal in response to moving the first control member includes detecting the movement of the first control member in space using at least one motion sensor.

A method for performing a medical procedure includes controlling one or more medical instruments using the controller described above. In an embodiment, the medical procedure includes one or more of laparoscopic surgery, natural orifice surgery, minimally-invasive surgery, prenatal surgery, intrauterine surgery, microscopic surgery, interventional radiology, interventional cardiology, endoscopy, cystoscopy, bronchoscopy, and colonoscopy. In an embodiment, the medical procedure utilizes one or more of Hansen robotic control, Da Vinci robotic control, three dimensional image guidance, and four dimensional image guidance.

A method for controlling a vehicle includes controlling one or more vehicle subsystems using the controller described above. In an embodiment, the vehicle includes one or more of an unmanned aerial vehicle, an unmanned submersible vehicle, a heavy mechanized vehicle, a piloted aircraft, a helicopter, a spacecraft, a spacecraft docking system, and a general aviation system.

A method for controlling a military system includes controlling one or more military subsystems using the controller described above. In an embodiment, the military system includes one or more of a weapons-targeting system, counter-improvised-explosive-device system, an air-to-air refueling system, and an explosives handling system.

A method for controlling an industrial system includes controlling one or more industrial subsystems using the controller described above. In an embodiment, the industrial system includes one or more of an oil exploration system, an overhead crane, a cherry picker, a boom lift, a basket crane, an industrial lift, a firefighting system, a dangerous materials handling system (including, without limitation, nuclear or biological materials handling systems), a metallurgical handling or foundry system, a steel or metals manufacturing system, a high-temperature handling or processing system, an explosives or ordinance handling system, and a waste management system.

A method for controlling a consumer device system includes controlling one or more consumer device subsystems using the controller described above. In an embodiment, the consumer device system includes one or more of a consumer electronics device, a video game console, a three-dimensional computer navigation system, a radio-controlled vehicle, and a three-dimensional computer-aided drafting system.

BRIEF DESCRIPTION OF THE DRAWINGS

For promoting an understanding of the principles of the invention, reference will now be made to the embodiments, or examples, illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one of ordinary skill in the art to which the invention relates.

The following drawings form part of the present specification and are included to demonstrate certain aspects of the present invention. The invention may be better understood by reference to the following description taken in conjunction with the accompanying drawings, in which like reference numerals identify like elements, and in which:

FIG. 2B is a rear-perspective view illustrating an embodiment of the controller of FIG. 2A;

FIG. 2C is a side view illustrating an embodiment of the controller of FIG. 2A;

FIG. 20 is a cross-sectional view illustrating an embodiment of the controller of FIG. 2A;

FIG. 2E is a rear view illustrating an embodiment of the controller of FIG. 2A;

FIG. 2G is a top view illustrating an embodiment of the controller of FIG. 2A;

FIG. 3A is a front-perspective view illustrating an embodiment of a controller;

FIG. 3B is a side-perspective view illustrating an embodiment of the controller of FIG. 3A;

FIG. 7B is a front view illustrating an embodiment of the controller of FIG. 7A;

FIG. 8A is a side view illustrating an embodiment of a controller;

FIG. 9A is a side view illustrating an embodiment of a controller; and

FIG. 9B is a top view illustrating an embodiment of the controller of FIG. 8A.

DESCRIPTION OF ILLUSTRATIVE EMBODIMENTS

Figure 1:
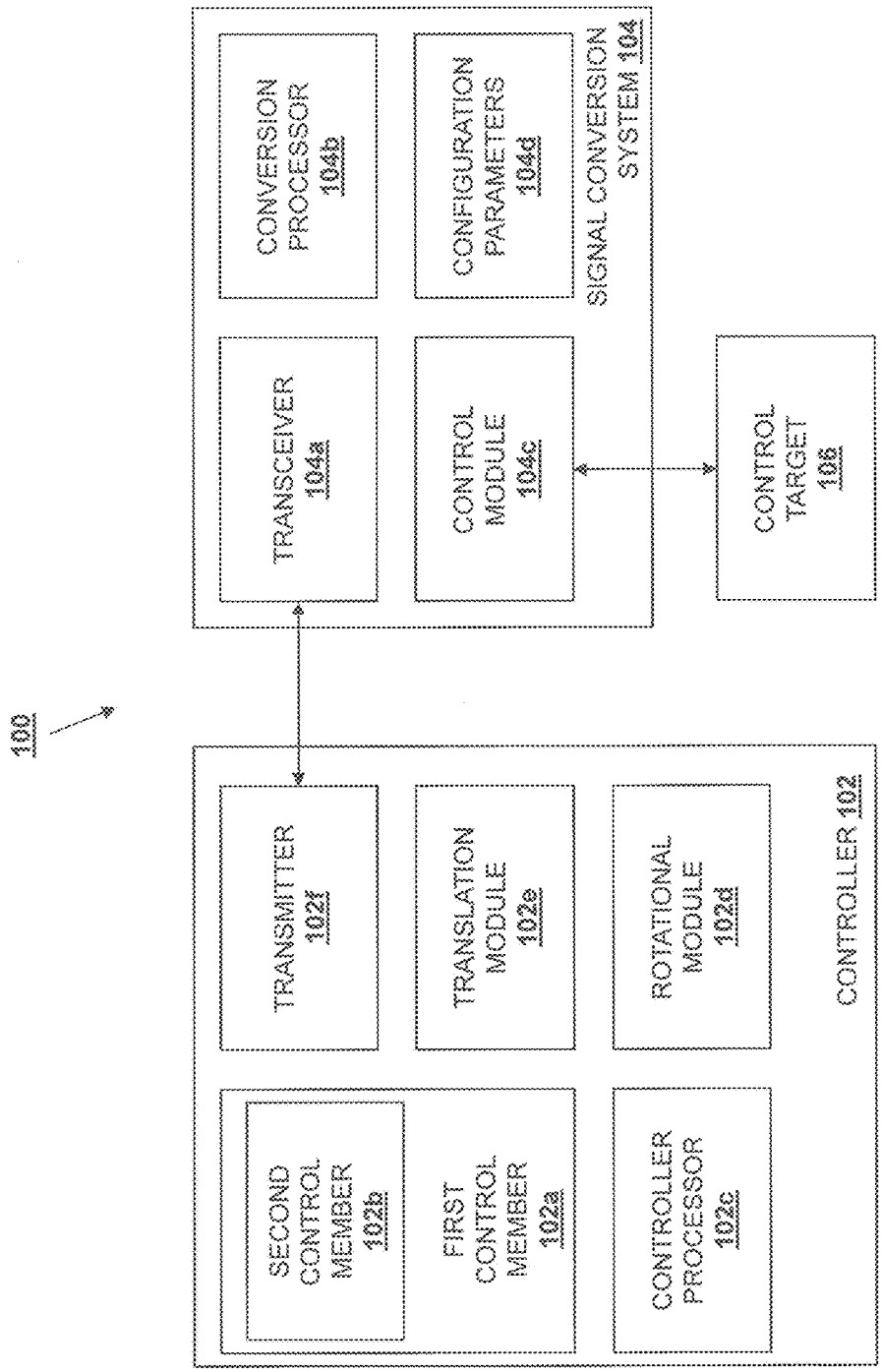
FIG. 1 is a schematic view of an embodiment of a control system.

In the drawings and description that follows, the drawings are not necessarily to scale. Certain features of the invention may be shown exaggerated in scale or in somewhat schematic form and some details of conventional elements may not be shown in the interest of clarity and conciseness. The present disclosure is susceptible to embodiments of different forms. Specific embodiments are described in detail and are shown in the drawings, with the understanding that the present disclosure is to be considered an exemplification of the principles of the invention, and is not intended to limit the invention to that illustrated and described herein. It is to be fully recognized that the different teachings of the embodiments discussed below may be employed separately or in any suitable combination to produce desired results. The various characteristics mentioned above, as well as other features and characteristics described in more detail below, will be readily apparent to those skilled in the art upon reading the following description of illustrative embodiments of the invention, and by referring to the drawings that accompany the specification.

Conventionally, multiple discrete controllers are utilized to allow a user to control a control target having more than three degrees of freedom. Furthermore, multiple discrete controllers have been required for any conventional control system that controls a control target having six degrees of freedom. For example, a set of independent controllers (e.g., joysticks, control columns, cyclic sticks, foot pedals, and/or other independent controllers as may be known by one or more of ordinary skill in the art) may be provided to receive a variety of different rotational parameters (e.g., pitch, yaw, and roll) from a user for a control target (e.g., an aircraft, submersible vehicles, spacecraft, a control target in a virtual environment, and/or a variety of other control targets as may be known by one or more of ordinary skill in the art), while a set of independent controllers may be provided to control other navigational parameters such as translation (e.g., x-, y-, and z-axis movement) in a three-dimensional (3D) space, velocity, acceleration, and/or a variety of other navigational parameters as may be known by one or more of ordinary skill in the art.

The present disclosure describes several embodiments of a control system that allows a user to control a control target in six DOF (6-DOF) using a single controller. In one embodiment, a unified hand controller may include a first control member for receiving rotational inputs (e.g., pitch, yaw, and roll) and a second control member that extends from the first control member and that is for receiving translational inputs (e.g., movement along x, y, and z axes). As described in further detail below, the first control member and the second control member on the unified hand controller may be repositioned by a user using a single hand to control the control target in 6-DOF.

Referring initially to FIG. 1, an embodiment of a control system 100 is illustrated. The embodiment of the control system 100 illustrated and described below is directed to a control system for controlling a control target in 6-DOF. The control system 100 includes a controller 102 that is coupled to a signal conversion system 104 that is further coupled to a control target 106. In an embodiment, the control target 106 may include end effectors (e.g., the end of a robotic forceps, a robotic arm and effector with snarks), camera field-of-views (e.g., including a camera center field-of-view and zoom), vehicle velocity vectors, etc. While the controller 102 and the signal conversion system 104 are illustrated separately, one of ordinary skill in the art will recognize that some or all of the controller 102 and the signal conversion system 104 may be combined without departing from the scope of the present disclosure. The controller 102 includes a first control member 102a and a second control member 102b that is located on the first control member 102a. A controller processor 102c is coupled to each of the first control member 102a and the second control member 102b. In an embodiment, the controller processor 102c may be a central processing unit, a programmable logic controller, and/or a variety of other processors as may be known by one or more of ordinary skill in the art. The controller processor 102c is also coupled to each of a rotational module 102d, a translation module 102e, and a transmitter 102f. While not illustrated or described in any further detail, other connections and coupling may exist between the first control member 102a, the second control member 102b, the controller processor 102c, the rotation module 102d, the translation module 102e, and the transmitter 102f while remaining within the scope of the present disclosure. Furthermore, components of the controller may be combined or substituted with other components as may be known by one or more of ordinary skill in the art while remaining with the scope of the present disclosure.

The signal conversion system 104 in the control system 100 includes a transceiver 104a that may couple to the transmitter 102f in the controller 102 through a wired connection, a wireless connection, and/or a variety of other connections as may be known by one or more of ordinary skill in the art. A conversion processor 104b is coupled to the transceiver 104a, a control module 104c, and configuration parameters 104d that may be included on a memory, a storage device, and/or other computer-readable mediums as may be known by one or more of ordinary skill in the art. In an embodiment, the conversion processor 104b may be a central processing unit, a programmable logic controller, and/or a variety of other processors known to those of ordinary skill in the art. While not illustrated or described in any further detail, other connections and coupling may exist between the transceiver 104a, the conversion processor 104b, the control module 104c, and the configuration parameters 104d while remaining within the scope of the present disclosure. Furthermore, components of the signal conversion system 104 may be combined or substituted with other components as may be known by one or more of ordinary skill in the art while remaining with the scope of the present disclosure. The control module 104c may be coupled to the control target 106 through a wired connection, a wireless connection, and/or a variety of other connections as may be known by one or more of ordinary skill in the art.

In an embodiment, the controller 102 is configured to receive input from a user through the first control member 102a and/or the second control member 102b and transmit a signal based on the input. For example, the controller 102 may be provided as a "joystick" for navigating in a virtual environment (e.g., in a video game, on a real-world simulator, as part of a remote control virtual/real-world control system, and/or in a variety of other virtual environments as may be known by one or more of ordinary skill in the art.) In another example, the controller 102 may be provided as a control stick for controlling a vehicle (e.g., an aircraft, a submersible, a spacecraft, and/or a variety of other vehicles as may be known by one or more of ordinary skill in the art). In another example, the controller 102 may be provided as a control stick for controlling a robot or other non-vehicle device (e.g., a surgical device, an assembly device, and/or variety of other non-vehicle devices known to one of ordinary skill in the art).

In the embodiment discussed in further detail below, the controller 102 includes a control stick as the first control member 102a that is configured to be repositioned by the user. The repositioning of the control stick first control member 102a allows the user to provide rotational inputs using the first control member 102a that include pitch inputs, yaw inputs, and roll inputs, and causes the controller processor 102c to output rotational movement output signals including pitch movement output signals, a yaw movement output signals, and roll movement output signals. In particular, tilting the control stick first control member 102a forward and backward may provide the pitch input that produces the pitch movement output signal, rotating the control stick first control member 102a left and right about its longitudinal axis may provide the yaw input that produces the yaw movement output signal, and tilting the control stick first control member 102a side to side may provide the roll input that produces the roll movement output signal. As discussed below, the movement output signals that result from the repositioning of the first control member 102a may be reconfigured from that discussed above such that similar movements of the first control member 102a to those discussed above result in different inputs and movement output signals (e.g., tilting the control stick first control member 102a side to side may be configured to provide the yaw input that produces the yaw movement output signal while rotating the control stick first control member 102a about its longitudinal axis may be configured provide the roll input that produces the roll movement output signal.)

Rotational inputs using the control stick first control member 102a may be detected and/or measured using the rotational module 102d. For example, the rotational module 102d may include displacement detectors for detecting the displacement of the control stick first control member 102a from a starting position as one or more of the pitch inputs, yaw inputs, and roll inputs discussed above. Displacement detectors may include photo detectors for detecting light beams, rotary and/or linear potentiometers, inductively coupled coils, physical actuators, gyroscopes, switches, transducers, and/or a variety of other displacement detectors as may be known by one or more of ordinary skill in the art. In some embodiments, the rotational module 102d may include accelerometers for detecting the displacement of the control stick first control member 102a from a starting position in space. For example, the accelerometers may each measure the proper acceleration of the control stick first control member 102a with respect to an inertial frame of reference.

In other embodiments, inputs using the control stick first control member 102a may be detected and/or measured using breakout switches, transducers, and/or direct switches for each of the three ranges of motion (e.g., front to back, side to side, and rotation about a longitudinal axis) of the control stick first control member 102a. For example, breakout switches may be used to detect when the control stick first control member 102a is initially moved (e.g., 2°) from a null position for each range of rotation, transducers may provide a signal that is proportional to the displacement of the control stick first control member 102a for each range of motion, and direct switches may detect when the control stick first control member 102a is further moved (e.g., 12°) from the null position for each range of motion. The breakout switches and direct switches may also allow for acceleration of the control stick first control member 102a to be detected. In an embodiment, redundant detectors and/or switches may be provided in the controller 102 to ensure that the control system 100 is fault tolerant.

In the embodiment discussed in further detail below, the second control member 102b extends from a top, distal portion of the control stick first control member 102a and is configured to be repositioned by the user independently from and relative to the control stick first control member 102a. The repositioning of the second control member 102b discussed below allows the user to provide translational inputs using the second control member 102b that include x-axis inputs, y-axis inputs, and z-axis inputs, and causes the control processor 102c to output a translational movement output signals including x-axis movement output signals, y-axis movement output signals, and z-axis movement output signals. For example, tilting the second control member 102b forward and backward may provide the x-axis input that produces the x-axis movement output signal, tilting the second control member 102b side to side may provide the y-axis input that produces the y-axis movement output signal, and moving the second control member 102b up and down may provide the z-axis input that produces the z-axis movement output signal. As discussed below, the signals that result from the repositioning of the second control member 102b may be reconfigured from that discussed above such that similar movements of the second control member 102b to those discussed above result in different inputs and movement output signals (e.g., tilting the second control member 102b forward and backward may be configured to provide the z-axis input that produces the z-axis movement output signal while moving the second control member 102b up and down may be configured to provide the x-axis input that produces the x-axis movement output signal.) In an embodiment, the second control member 102b is configured to be repositioned solely by a thumb of the user while the user is gripping the control stick first control member 102a with the hand that includes that thumb.

Translational inputs using the second control member 102b may be detected and/or measured using the translation module 102e. For example, the translation module 102e may include translational detectors for detecting the displacement of the second control member 102b from a starting position as one or more of the x-axis inputs, y-axis inputs, and z-axis inputs discussed above. Translation detectors may include physical actuators, translational accelerometers, and/or a variety of other translation detectors as may be known by one or more of ordinary skill in the art (e.g., many of the detectors and switches discussed above for detecting and/or measuring rotational input may be repurposed for detecting and/or measuring translation input.)

In an embodiment, the controller processor 102c of the controller 102 is configured to generate control signals to be transmitted by the transmitter 102f. As discussed above, the controller processor 102c may be configured to generate a control signal based on one or more rotational inputs detected and/or measured by the rotational module 102d and/or one or more translational inputs detected and/or measured by the translation module 102e. Those control signal generated by the controller processor 102c may include parameters defining movement output signals for one or more of 6-DOF (i.e., pitch, yaw, roll, movement along an x-axis, movement along a y-axis, movement along a z-axis). In several embodiments, a discrete control signal type (e.g., yaw output signals, pitch output signals, roll output signals, x-axis movement output signals, y-axis movement output signals, and z-axis movement output signals) is produced for each discrete predefined movement (e.g., first control member 102a movement for providing pitch input, first control member 102a movement for providing yaw input, first control member 102a movement for providing roll input, second control member 102b movement for providing x-axis input, second control member 102b movement for providing y-axis input, and second control member 102b movement for providing z-axis input) that produces that discrete control signal. Beyond 6-DOF control, discrete features such as ON/OFF, trim, and other multi-function commands may be transmitted to the control target. Conversely, data or feedback may be received on the controller 102 (e.g., an indicator such as an LED may be illuminated green to indicate the controller 102 is on.)

In an embodiment, the transmitter 102f of the controller 102 is configured to transmit the control signal through a wired or wireless connection. For example, the control signal may be one or more of a radio frequency ("RF") signal, an infrared ("IR") signal, a visible light signal, and/or a variety of other control signals as may be known by one or more of ordinary skill in the art. In some embodiments, the transmitter 102f may be a BLUETOOTH® transmitter configured to transmit the control signal as an RF signal according to the BLUETOOTH® protocol (BLUETOOTH® is a registered trademark of the Bluetooth Special Interest Group, a privately held, not-for-profit trade association headquartered in Kirkland, Wash., USA).

In an embodiment, the transceiver 104a of the signal conversion system 104 is configured to receive the control signal transmitted by the transmitter 102f of the controller 102 through a wired or wireless connection, discussed above, and provide the received control signal to the conversion processor 104b of the signal conversion system 104.

In an embodiment, the conversion processor 104b is configured to process the control signals received from the controller 102. For example, the conversion processor 104b may be coupled to a computer-readable medium including instructions that, when executed by the conversion processor 104b, cause the conversion processor 104b to provide a control program that is configured to convert the control signal into movement commands and use the control module 104c of the signal conversion system 104 to control the control target 106 according to the movement commands. In an embodiment, the conversion processor 104b may convert the control signal into movement commands for a virtual three-dimensional ("3D") environment (e.g., a virtual representation of surgical patient, a video game, a simulator, and/or a variety of other virtual 3D environments as may be known by one or more of ordinary skill in the art). Thus, the control target 106 may exist in a virtual space, and the user may be provided a point of view or a virtual representation of the virtual environment from a point of view inside the control target (i.e., the control system 100 may include a display that provides the user a point of view from the control target in the virtual environment). In another example, the control target 106 may be a physical device such as a robot, an end effector, a surgical tool, a lifting system, etc., and/or a variety of steerable mechanical devices, including, without limitation, vehicles such as unmanned or remotely-piloted vehicles (e.g., "drones"); manned, unmanned, or remotely-piloted vehicles and landcraft; manned, unmanned, or remotely-piloted aircraft; manned, unmanned, or remotely-piloted watercraft; manned, unmanned, or remotely-piloted submersibles; as well as manned, unmanned, or remotely-piloted space vehicles, rocketry, satellites, and such like.

In an embodiment, the control module 104c of the signal conversion system 104 is configured to control movement of the control target 106 based on the movement commands provided from the control program in signal conversion system 104. In some embodiments, if the control target 106 is in a virtual environment, the control module 104c may include an application programming interface (API) for moving a virtual representation or point of view within the virtual environment. API's may also provide the control module 104c with feedback from the virtual environment such as, for example, collision feedback. In some embodiments, feedback from the control target 106 may allow the control module 104c to automatically adjust the movement of the control target to, for example, avoid a collision with a designated region (e.g., objects in a real or virtual environment, critical regions of a real or virtual patient, etc.). In other embodiments, if the control target 106 is a physical device, the control module 104c may include one or more controllers for controlling the movement of the physical device. For example, the signal conversion system 104 may be installed on-board a vehicle, and the control module 104c may include a variety of physical controllers for controlling various propulsion and/or steering mechanisms of the vehicle.

In an embodiment, the signal conversion system 104 includes operating parameters 104d for use by the conversion processor 104b when generating movement commands using the signals from the controller 102. Operating parameters may include, but are not limited to, gains (i.e., sensitivity), rates of onset (i.e., lag), deadbands (i.e., neutral), limits (i.e., maximum angular displacement), and/or a variety of other operating parameters as may be known by one or more of ordinary skill in the art. In an embodiment, the gains of the first control member 102a and the second control member 102b may be independently defined by a user. In this example, the second control member 102b may have increased sensitivity compared to the control stick first control member 102a to compensate, for example, for the second control member 102b having a smaller range of motion that the control stick first control member 102a. Similarly, the rates of onset for the first control member 102a and the second control member 102b may be defined independently to determine the amount of time that should pass (i.e., lag) before a repositioning of the first control member 102a and the second control member 102b should be converted to actual movement of the control target 106. The limits and deadbands of the first control member 102a and the second control member 102b may be independently defined as well by calibrating the neutral and maximal positions of each.

In an embodiment, operating parameters may also define how signals sent from the controller 102 in response to the different movements of the first control member 102*a* and the second control member 102*b* are translated into movement commands that are sent to the control target. As discussed above, particular movements of the first control member 102*a* may produce pitch, yaw, and roll rotational movement output signals, while particular movements of the second control member 102*b* may produce x-axis, y-axis, and z-axis translational movement output signals. In an embodiment, the operating parameters may define which movement commands are sent to the control target 106 in response to movements and resulting movement output signals from the first control member 102*a* and second control member 102*b*.

In some embodiments, the operating parameters 104*d* may be received from an external computing device (not shown) operated by the user. For example, the external computing device may be preconfigured with software for interfacing with the controller 102 and/or the signal conversion system 104. In other embodiments, the operating parameters 104*d* may be input directly by a user using a display screen included with the controller 102 or the signal conversion system 104. For example, the first control member 102*a* and/or second control member 102*b* may be used to navigate a configuration menu for defining the operating parameters 104*d*.

Figure 2A:
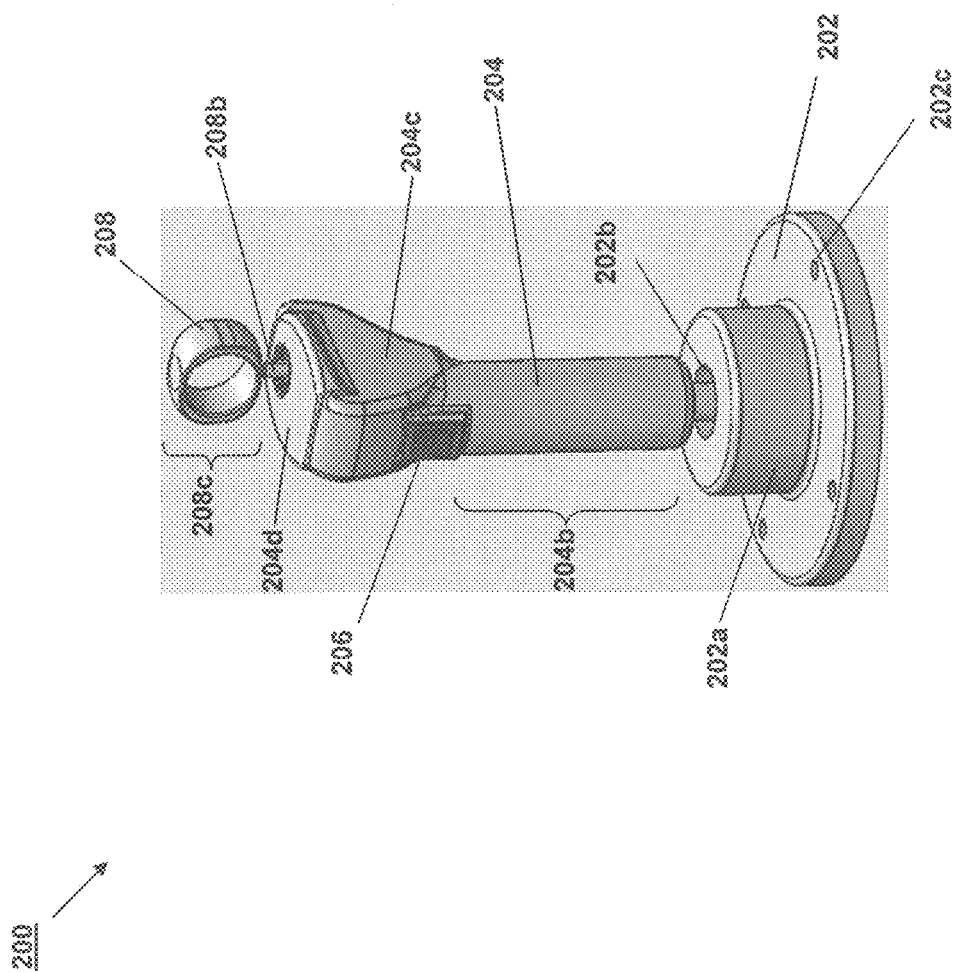
FIG. 2A is a front-perspective view illustrating an embodiment of a controller.

Referring now to FIG. 2A, FIG. 2B, FIG. 2C, FIG. 2D, FIG. 2E, FIG. 2F, and FIG. 2G, an illustrative embodiment of an exemplary controller 200 is shown. In an embodiment, the controller 200 may be the controller 102 discussed above with reference to FIG. 1. The controller 200 includes a base 202 including a first control member mount 202*a* that extends from the base 202 and defines a first control member mount cavity 202*b*. The base 202 may be mounted to a support using, for example, apertures 202*c* that are located in a spaced apart orientation about the circumference of the base 202 and that may be configured to accept a fastening member such as a screw. Alternatively, a dovetail fitting with a guide-installation and release or other mechanical, magnetic, or other adhesive fixation mechanism known in the art may be utilized. A first control member 204, which may be the first control member 102*a* discussed above with reference to FIG. 1, is coupled to the base 200 through a base coupling member 204*a* that is positioned in the first control member mount cavity 202*b*, as illustrated in FIG. 2D. While in the illustrated embodiment, the coupling between the base coupling member 204*a* and first control member mount 202*a* is shown and described as a ball-joint coupling, one of ordinary skill in the art will recognize that a variety of other couplings between the base 202 and the first control member 204 will fall within the scope of the present disclosure. In an embodiment, a resilient member 205 such as, for example, a spring, may be positioned between the first control member 204 and the base 202 in the first control member mount cavity 202*b* in order to provide resilient movement up or down along the longitudinal axis of the first control member 204. Furthermore, a resilient member may be provided opposite the base coupling member 204*a* from the resilient member 205 in order to limit upward movement of the first control member 204. Furthermore, as can be seen in FIG. 2A and FIG. 2B, the entrance to the first control member mount cavity 202*b* may be smaller than the base coupling member 204*a* such that the first control member 204 is secured to the base 202.

The first control member 204 includes an elongated first section 204*b* that extends from the base coupling member 204*a*. The first control member 204 also includes a grip portion 204*c* that is coupled to the first section 204*b* of the first control member 204 opposite the first section 204*b* from the base coupling member 204*a*. The grip portion 204*c* of the first control member 204 includes a top surface 204*d* that is located opposite the grip portion 204*c* from the first section of 204*b* of the first control member 204. In the illustrated embodiments, the top surface 204*d* of the grip portion 204*c* is also a top surface of the first control member 204. The grip portion 204*c* defines a second control member mount cavity 204*e* that extends into the grip portion 204*c* from the top surface 204*d*. A control button 206 is located on the first control member 204 at the junction of the first section 204*b* and the grip portion 204*c*. While a single control button 206 is illustrated, one of ordinary skill in the art will recognize that a plurality of control buttons may be provided at different locations on the first control member 204 without departing from the scope of the present disclosure.

A second control member 208, which may be the second control member 102*b* discussed above with reference to FIG. 1, is coupled to the first control member 204 through a first control member coupling member 208*a* that is positioned in the second control member mount cavity 204*e*, as illustrated in FIG. 2D. While in the illustrated embodiment, the coupling between the first control member coupling member 208*a* and first control member 204 is shown and described as a ball-joint coupling, one of ordinary skill in the art will recognize that a variety of other couplings between the first control member 204 and the second control member 208 will fall within the scope of the present disclosure. In an embodiment, a resilient member 209 such as, for example, a spring, may be positioned between the second control member 208 and the first control member 204 in the second control member mount cavity 204*e* in order to provide resilient movement up or down in a direction that is generally perpendicular to the top surface 204*d* of the grip portion 204*c*. Furthermore, as can be seen in FIG. 2A and FIG. 2B, the entrance to the second control member mount cavity 204*e* may be smaller than the first control member coupling member 208*a* such that the second control member 208 is secured to and extends from the first control member 204.

The second control member 208 includes a support portion 208*b* that extends from the first control member coupling member 208*a*. The second control member 208 also includes an actuation portion 208*c* that is coupled to the support portion 208*b* of the first control member 204 opposite the support portion 208*b* the first control member coupling member 208*a*. In the illustrated embodiments, the actuation portion 208*c* of the second control member 208 defines a thumb channel that extends through the actuation portion 208*c* of the second control member 208. While a specific actuation portion 208*c* is illustrated, one of ordinary skill in the art will recognize that the actuation portion 208*c* may have a different structure and include a variety of other features while remaining within the scope of the present disclosure.

FIG. 2D illustrates cabling 210 that extends through the controller 200 from the second control member 208, through the first control member 204 (with a connection to the control button 206), and to the base 202. While not illustrated for clarity, one of ordinary skill in the art will recognize that some or all of the features of the controller 102, described above with reference to FIG. 1, may be included in the controller 200. For example, the features of the rotational module 102*d* and the translation module 102*e* such as the detectors, switches, accelerometers, and/or other components for detecting movement of the first control member 204 and the second control member 208 may be positioned adjacent the base coupling member 204a and the first control member coupling member 208a in order to detect and measure the movement of the first control member 204 and the second control member 208, as discussed above. Furthermore, the controller processor 102c and the transmitter 102f may be positioned, for example, in the base 202. In an embodiment, a cord including a connector may be coupled to the cabling 210 and operable to connect the controller 200 to a control system (e.g., the control system 100). In another embodiment, the transmitter 102f may allow wireless communication between the controller 200 and a control system, as discussed above.

FIG. 3A and FIG. 3B illustrate an embodiment of a controller 300 that is substantially similar to the controller 200, discussed above, but with the removal of the base 202 and the base coupling member 204a. As discussed in further detail below, while not illustrated, one of ordinary skill in the art will recognize that some or all of the features of the controller 102, described above with reference to FIG. 1, may be included in the controller 300 such as, for example, features of the rotational module 102d including accelerometers or other devices for detecting movement of the first control member 204 in space. Furthermore, the transmitter 102f may be located in the first control member 204 of the controller 300 for providing wireless communication between the controller 300 and a control system, as discussed above.

In the illustrated embodiment, the second control member 208 of the controllers 200 and/or 300 is positioned on the top surface 204d of the apical grip portion 204c. The apical grip portion 204c for the index finger to wrap around and/or the distal group section 204b for the third through fifth fingers to wrap around of the first control member are configured to be grasped by a hand of a user to allow for repositioning of the first control member 204 (e.g., about its coupling to the base 202 for the controller 200, or in space for the controller 300) to provide the rotational inputs as discussed above. The second control member 208 is configured to be engaged by a thumb of the hand of the user (e.g., through the thumb channel) that is grasping the apical grip portion 204c and/or the distal grip section 204b of the first control member 204 to allow the thumb to reposition the second control member 208 about its coupling to the first control member 204 to provide the translational inputs discussed above. In the illustrated embodiment, the thumb channel enhances the ability of a user to reposition the second control member 208 up and down (i.e., generally perpendicular to the top surface 204d of the grip portion 204c) using the thumb, in addition to providing a full range-of-motion in a two-dimensional plane (e.g., forward, backwards, left, right) that is parallel with the top surface 204d of the grip portion 204c of the first control member 204.

Figure 4A:
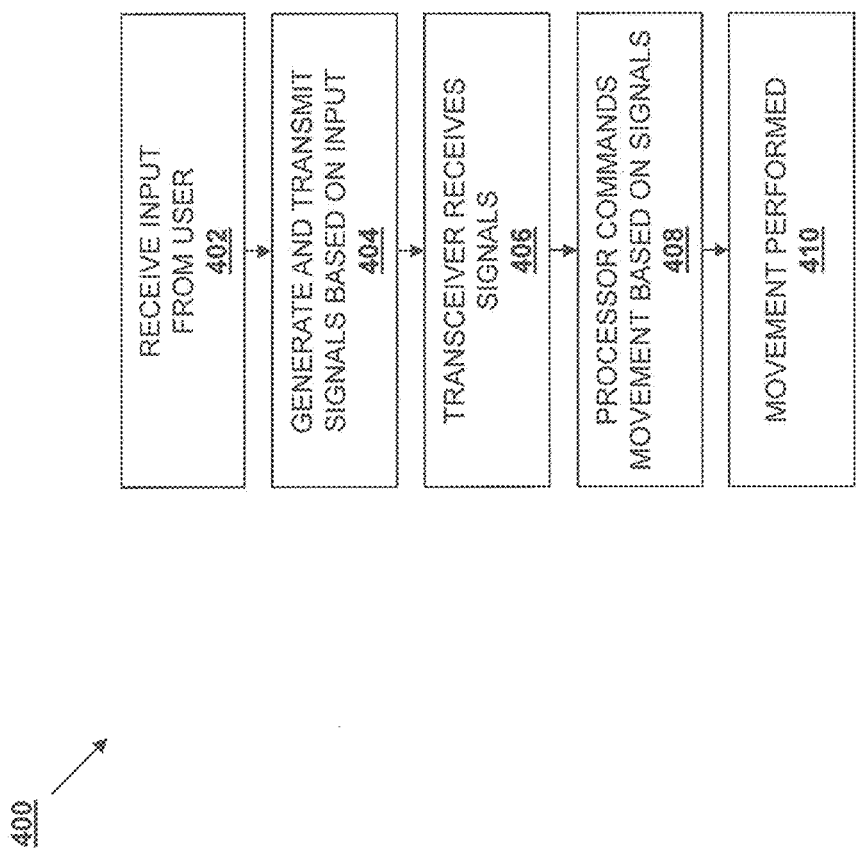
FIG. 4A is a flowchart illustrating an embodiment of a method for controlling a control target.
Figure 4B:
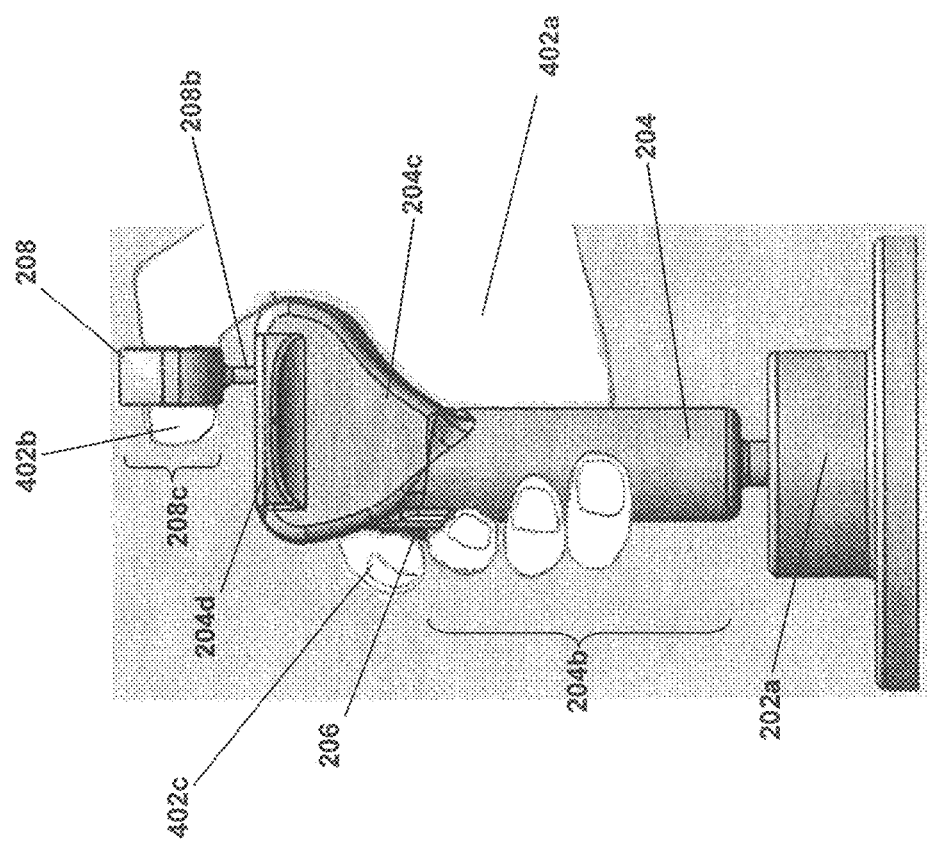
FIG. 4B is a side view illustrating an embodiment of a user using the controller depicted in FIG. 2A-FIG. 2G with a single hand.

Referring now to FIG. 4A and FIG. 4B, a method 400 for controlling a control target is illustrated. As is the case with the other methods described herein, various embodiments may not include all of the steps described below, may include additional steps, and may sequence the steps differently. Accordingly, the specific arrangement of steps shown in FIG. 4A should not be construed as limiting the scope of controlling the movement of a control target.

The method 400 begins at block 402 where an input is received from a user. As illustrated in FIG. 4B, a user may grasp the first control member 204 with a hand 402a, while extending a thumb 402b through the thumb channel defined by the second control member 208. Furthermore, the user may position a finger 402c over the control button 206. One of ordinary skill in the art will recognize that while a specific embodiment having the second control member 208 positioned for thumb actuation and control button 206 for finger actuation are illustrated, other embodiments that include repositioning of the second control member 208 (e.g., for actuation by a finger other than the thumb), repositioning of the control button 206 (e.g., for actuation by a finger other than the finger illustrated in FIG. 4B), additional control buttons, and a variety of other features will fall within the scope of the present disclosure.

In an embodiment, the input from the user at block 402 of the method 400 may include rotational inputs (i.e., a yaw input, a pitch input, and a roll input) and translational inputs (i.e., movement along an x-axis, a y-axis, and/or a z-axis) that are provided by the user using, for example, the controllers 102, 200, or 300. The user may reposition the first control member 204 to provide the rotational inputs and reposition the second control member 208 to provide the translational inputs. As illustrated in FIG. 4B, the controller 200 is "unified" in that it is capable of being operated by a single hand 402a of the user. In other words, the controller 200 allows the user to simultaneously provide rotational and translational inputs with a single hand without cross-coupling inputs (i.e., the inputs to the controller 200 are "pure"). As discussed above, the rotational and translational input may be detected using various devices such as photo detectors for detecting light beams, rotary and/or linear potentiometers, inductively coupled coils, physical actuators, gyroscopes, accelerometers, and a variety of other devices as may be known by one or more of ordinary skill in the art. A specific example of movements of the first control member 204 and the second control member 208 and their results on the control target 106 are discussed below, but as discussed above, any movements of the first control member 204 and the second control member 208 may be reprogrammed or repurposed to the desires of the user (including reprogramming references frames by swapping the coordinate systems based on the desires of a user), and thus the discussion below is merely exemplary of one embodiment of the present disclosure.

Figure 2F:
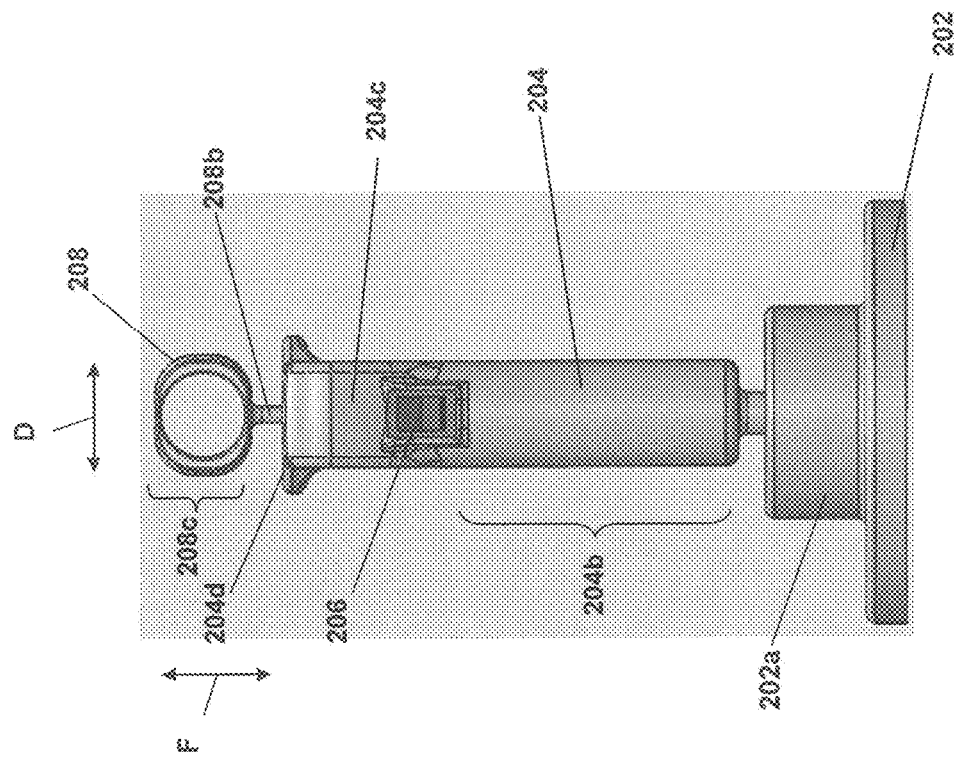
FIG. 2F is a front view illustrating an embodiment of the controller of FIG. 2A.

As illustrated in FIG. 2C, FIG. 2D, and FIG. 4B, the user may use his/her hand 402a to move the first control member 204 back and forth along a line A (e.g., on its coupling to the base 202 for the controller 200, by tilting the grip portion 204c of the first control member 204 along the line A relative to the bottom portion of the first control member 204 for the controller 300), in order to provide pitch inputs to the controller 200 or 300. As illustrated in FIG. 2G and FIG. 4B, the user may use his/her hand 402a to rotate the first control member 204 back and forth about its longitudinal axis on an arc B (e.g., on its coupling to the base 202 for the controller 200, by rotating the grip portion 204c of the first control member 204 in space for the controller 300), in order to provide yaw inputs to the controller 200 or 300. As illustrated in FIG. 2E, FIG. 2F, and FIG. 4B, the user may use their hand 402a to move the first control member 204 side to side along a line C (e.g., on its coupling to the base 202 for the controller 200, by tiling the grip portion 204c of the first control member 204 along the line B relative to the bottom portion of the first control member 204 for the controller 300), in order to provide roll inputs to the controller 200 or 300. Furthermore, additional inputs may be provided using other features of the controller 200. For example, the resilient member 205 may provide a neutral position of the first control member 204 such that compressing the resilient member 209 using the first control member 204 provides a first input and extending the resilient member 209 using the first control member 204 provides a second input.

As illustrated in FIG. 2E, FIG. 2F, FIG. 2G, and FIG. 4B, the user may use the thumb 402b to move the second control member 208 forwards and backwards along a line E (e.g., on its coupling to the first control member 204), in order to provide x-axis inputs to the controller 200 or 300. As illustrated in FIG. 2C, FIG. 2D, FIG. 2G, and FIG. 4B, the user may use the thumb 402b to move the second control member 208 back and forth along a line D (e.g., on its coupling to the first control member 204), in order to provide y-axis inputs to the controller 200 or 300. As illustrated in FIG. 2C, FIG. 2D, FIG. 2E, and FIG. 2F, and FIG. 4B, the user may use the thumb 402b to move the second control member 208 up and down along a line F (e.g., on its coupling to the first control member 204 including, in some embodiments, with resistance from the resilient member 209), in order to provide z-axis inputs to the controller 200 or 300. In an embodiment, the resilient member 209 may provide a neutral position of the second control member 208 such that compressing the resilient member 209 using the second control member 204 provides a first z-axis input for z-axis movement of the control target 106 in a first direction, and extending the resilient member 209 using the second control member 204 provides a second z-axis input for z-axis movement of the control target 106 in a second direction that is opposite the first direction.

The method 400 then proceeds to block 404 where a control signal is generated based on the user input received in block 402 and then transmitted. As discussed above, the controller processor 102e and the rotational module 102d may generate rotational movement output signals in response to detecting and/or measuring the rotational inputs discussed above, and the control processor 102c and the translation module 102e may generate translational movement output signals in response to detecting and/or measuring the translation inputs discussed above. Furthermore, control signals may include indications of absolute deflection or displacement of the control members, rate of deflection or displacement of the control members, duration of deflection or displacement of the control members, variance of the control members from a central deadband, and/or a variety of other control signals known in the art.) For example, control signals may be generated based on the rotational and/or translational input or inputs according to the BLUETOOTH® protocol. Once generated, the control signals may be transmitted as an RF signal by an RF transmitter according to the BLUETOOTH® protocol. Those skilled in the art will appreciate that an RF signal may be generated and transmitted according to a variety of other RF protocols such as the ZIGBEE® protocol, the Wireless USB protocol, etc. In other examples, the control signal may be transmitted as an IR signal, a visible light signal, or as some other signal suitable for transmitting the control information. (ZIGBEE® is a registered trademark of the ZigBee Alliance, an association of companies headquartered in San Ramon, Calif., USA).

The method 400 then proceeds to block 406 where a transceiver receives a signal generated and transmitted by the controller. In an embodiment, the transceiver 104a of the signal conversion system 104 receives the control signal generated and transmitted by the controller 102, 200, 300. In an embodiment in which the control signal is an RF signal, the transceiver 104a includes an RE sensor configured to receive a signal according to the appropriate protocol (e.g., BLUETOOTH®, ZIGBEE®, Wireless USB, etc.).

In other embodiments, the control signal may be transmitted over a wired connection. In this case, the transmitter 102f of the controller 102 and the transceiver 104a of the signal conversion system 104 may be physically connected by a cable such as a universal serial bus (USB) cable, serial cable, parallel cable, proprietary cable, etc.

The method 400 then proceeds to block 408 where control program provided by the conversion processor 104b of the signal conversion system 104 commands movement based on the control signals received in block 406. In an embodiment, the control program may convert the control signals to movement commands that may include rotational movement instructions and/or translational movement instructions based on the rotational movement output signals and/or translational movement output signals in the control signals. Other discrete features such as ON/OFF, camera zoom, share capture, and so on can also be relayed. For example, the movement commands may specify parameters for defining the movement of the control target 106 in one or more DOF. Using the example discussed above, if the user uses their hand 402a to move the first control member 204 back and forth along a line A (illustrated in FIG. 2C, FIG. 2D, and FIG. 4B), the resulting control signal may be used by the control program to generate a movement command including a pitch movement instruction for modifying a pitch of the control target 106. If the user uses their hand 402a to rotate the first control member 204 back and forth about its longitudinal axis about an arc B (illustrated in FIG. 2G and FIG. 4B), the resulting control signal may be used by the control program to generate a movement command including a yaw movement instruction for modifying a yaw of the control target 106. If the user uses their hand 402a to move the first control member 204 side to side along a line C (illustrated in FIG. 2E, FIG. 2F, and FIG. 4B), the resulting control signal may be used by the control program to generate a movement command including a roll movement instruction for modifying a roll of the control target 106.

Furthermore, if the user uses their thumb 402b to move the second control member 208 forward and backwards along a line E (illustrated in FIG. 2E, FIG. 2F, FIG. 2G, and FIG. 4B), the resulting control signal may be used by the control program to generate a movement command including an x-axis movement instruction for modifying the position of the control target 106 along an x-axis. If the user uses their thumb 402b to move the second control member 208 back and forth along a line E (illustrated in FIG. 2C, FIG. 2D, FIG. 2G, and FIG. 4B), the resulting control signal may be used by the control program to generate a movement command including a y-axis movement instruction for modifying the position of the control target 106 along a y-axis. If the user uses their thumb 402b to move the second control member 208 side to side along a line D (illustrated in FIG. 2C, FIG. 2D, FIG. 2E, FIG. 2F, and FIG. 4B), the resulting control signal may be used by the control program to generate a movement command including a z-axis movement instruction for modifying the position of the control target 106 along a z-axis.

The method 400 then proceeds to block 410 where the movement of the control target 106 is performed based on the movement commands. In an embodiment, a point of view or a virtual representation of the user may be moved in a virtual environment based on the movement commands at block 410 of the method 400. In another embodiment, an end effector, a propulsion mechanism, and/or a steering mechanism of a vehicle may be actuated based on the movement commands at block 410 of the method 400.

Figure 4C:
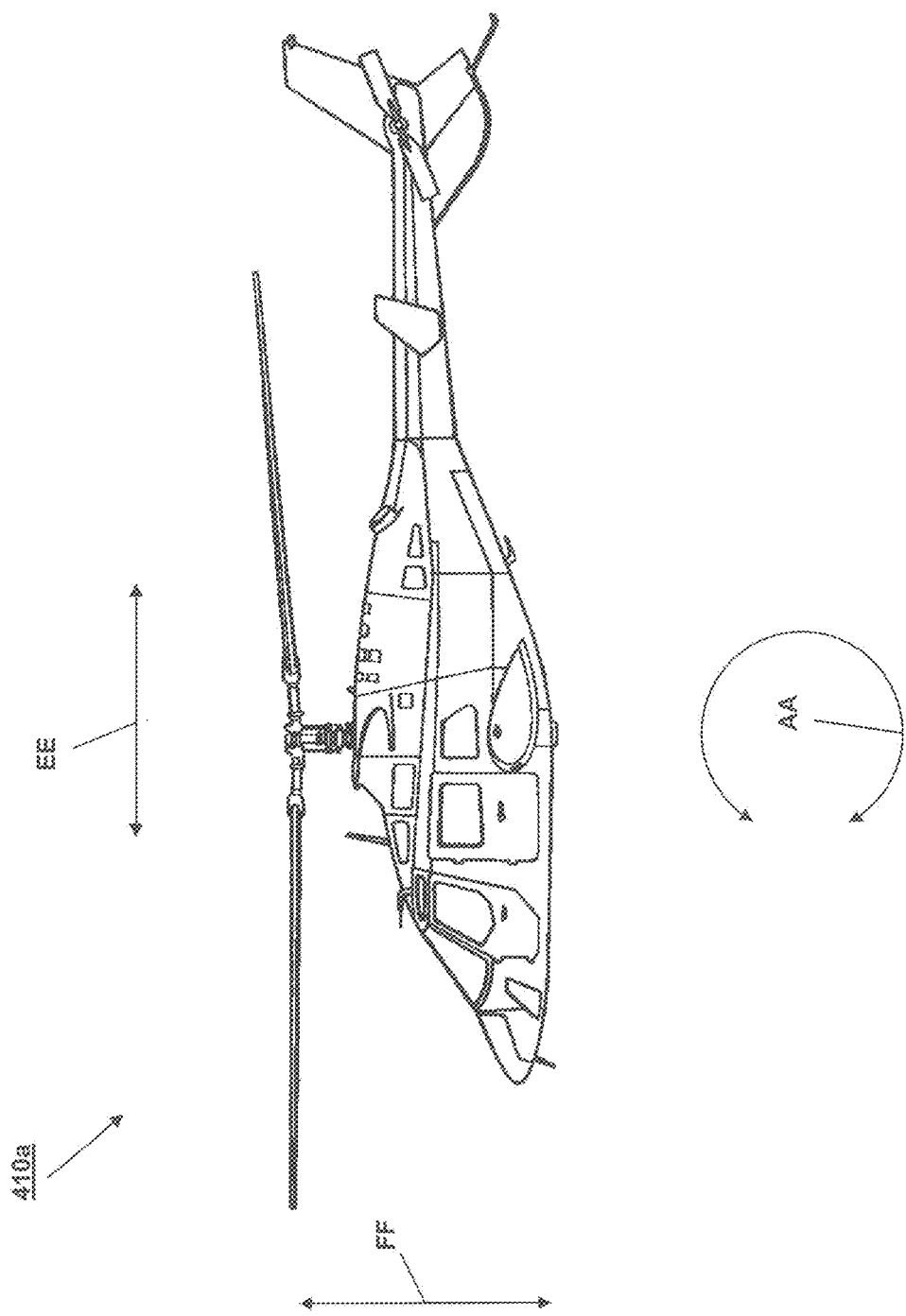
FIG. 4C is a side view illustrating an embodiment of a physical or virtual vehicle control target executing movements according to the method of FIG. 4A.
Figure 4D:
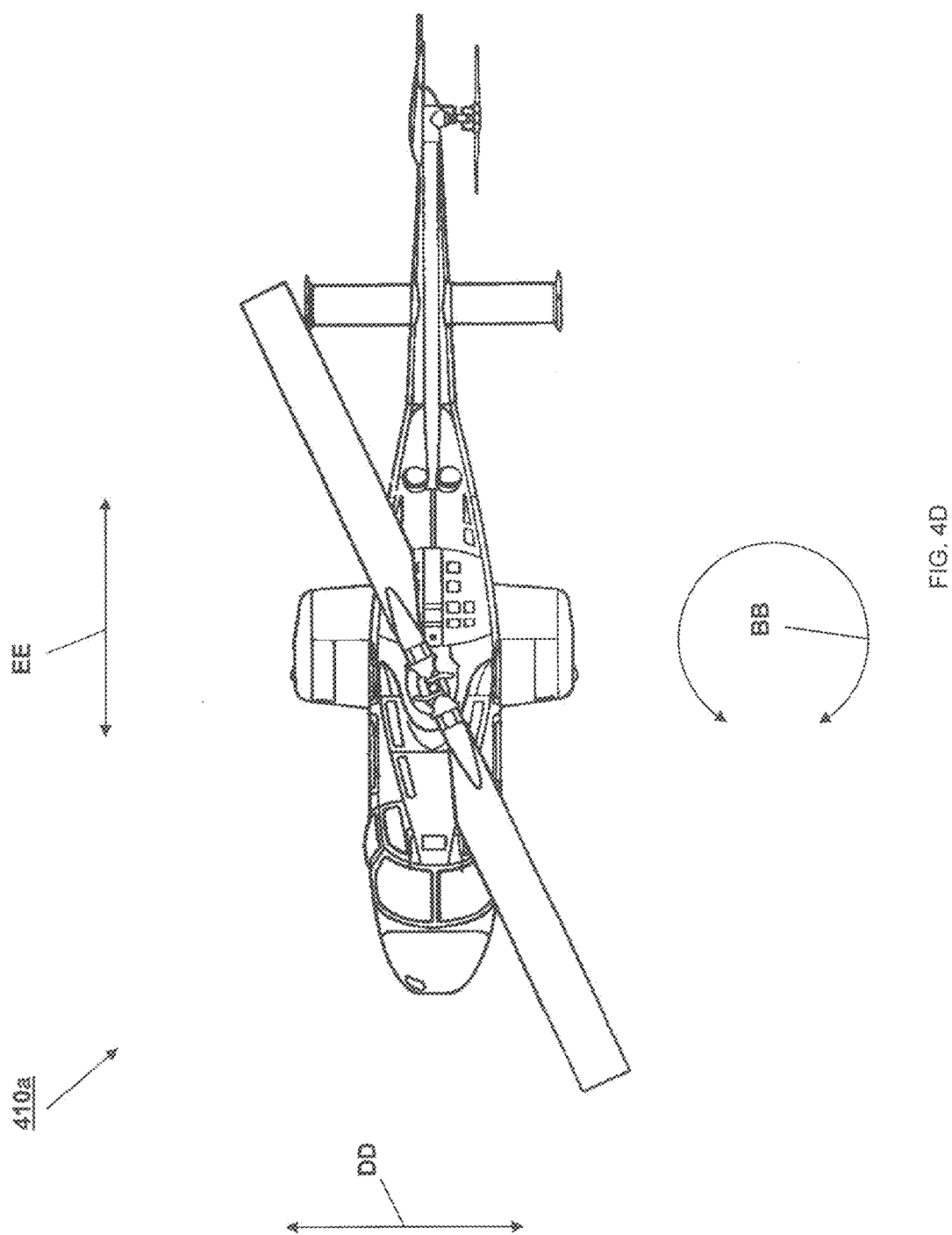
FIG. 4D is a top view illustrating an embodiment of the physical or virtual vehicle control target of FIG. 4C executing movements according to the method of FIG. 4A.
Figure 4E:
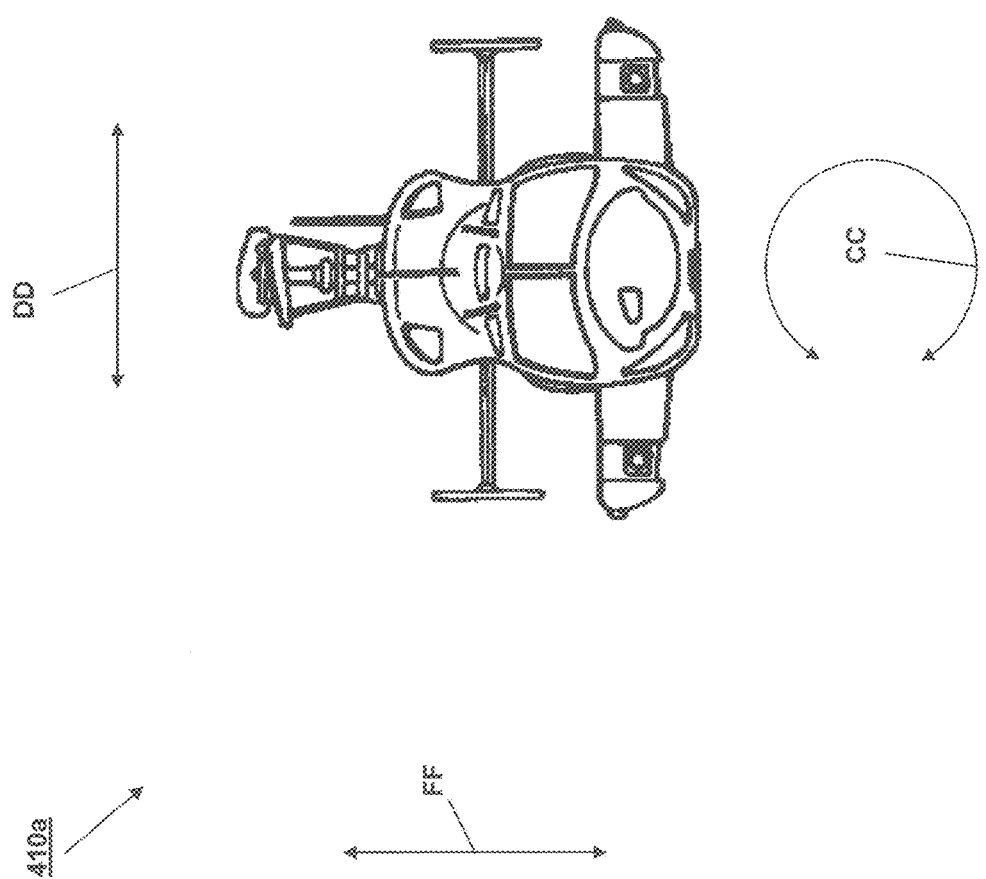
FIG. 4E is a front view illustrating an embodiment of the physical or virtual vehicle control target of FIG. 4C executing movements according to the method of FIG. 4A.

FIG. 4C, FIG. 4D, and FIG. 4E illustrate a control target 410a that may be, for example, the control target 106 discussed above, with reference to FIG. 1. As discussed above, the control target 410a may include a physical vehicle in which the user is located, a remotely operated vehicle where the user operates the vehicle remotely from the vehicle, a virtual vehicle operated by the user through the provision of a point-of-view to the user from within the virtual vehicle, and/or a variety of other control targets as may be known by one or more of ordinary skill in the art. Using the example above, if the user uses their hand 402a to move the first control member 204 back and forth along a line A (illustrated in FIG. 2C, FIG. 2D, and FIG. 4B), the movement command resulting from the control signal generated will cause the control target 410a to modify its pitch about an arc AA, illustrated in FIG. 4D. If the user uses their hand 402a to rotate the first control member 204 back and forth about its longitudinal axis about an arc B (illustrated in FIG. 2O and FIG. 4B), the movement command resulting from the control signal generated will cause the control target 410a to modify its yaw about an arc BB, illustrated in FIG. 4D. If the user uses their hand 402a to move the first control member 204 side to side along a line C (illustrated in FIG. 2E, FIG. 2F, and FIG. 4B), the movement command resulting from the control signal generated will cause the control target 410a to modify its roll about an arc CC, illustrated in FIG. 4E.

Furthermore, if the user uses his/her thumb 402b to move the second control member 208 forward and backwards along a line E (illustrated in FIG. 2E, FIG. 2F, FIG. 2G, and FIG. 4B), the movement command resulting from the control signal generated will cause the control target 410a to move along a line EE (i.e., its x-axis), illustrated in FIG. 4D and FIG. 4E. If the user uses his/her thumb 402b to move the second control member 208 side to side along a line D (illustrated in FIG. 2C, FIG. 2D, FIG. 2G, and FIG. 4B), the movement command resulting from the control signal generated will cause the control target 410a to move along a line DD (i.e., its y-axis), illustrated in FIG. 4C and FIG. 4D. If the user uses his/her thumb 402b to move the second control member 208 back and forth along a line F (illustrated in FIG. 2C, FIG. 2D, FIG. 2E, FIG. 2F, and FIG. 4B), the movement command resulting from the control signal generated will cause the control target 410a to move along a line FF (i.e., its z-axis), illustrated in FIG. 4C and FIG. 4E. In some embodiments, the control button 206 and/or other control buttons on the controller 102, 200, or 300 may be used to, for example, actuate other systems in the control target 410a (e.g., weapons systems.)

Figure 4F:
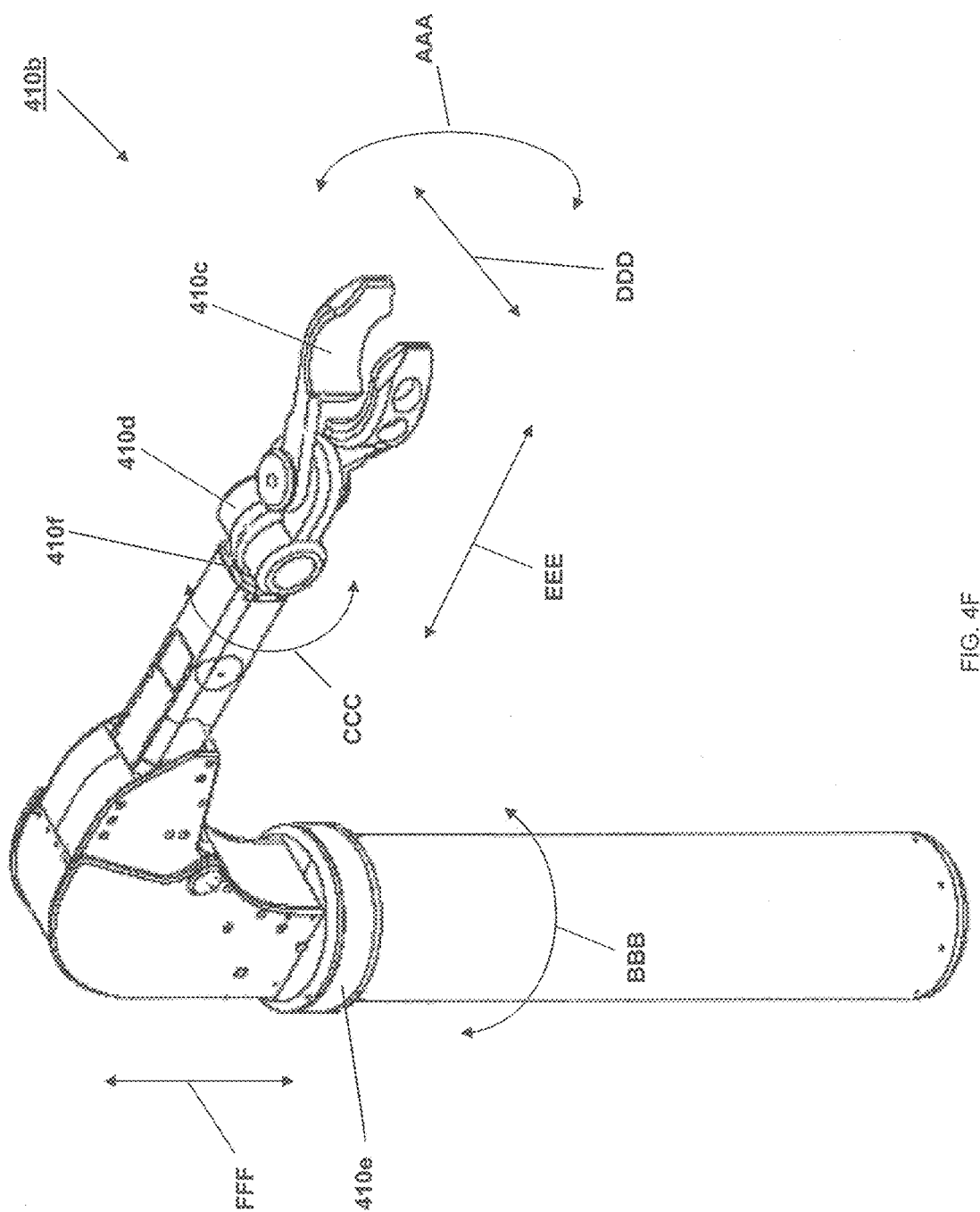
FIG. 4F is a perspective view illustrating an embodiment of a tool control target executing movements according to the method of FIG. 4A.

FIG. 4F illustrates a control target 410b that may be, for example, the control target 106 discussed above, with reference to FIG. 1. As discussed above, the control target 410b may include a physical device or other tool that executed movements according to signals sent from the controller 102, 200, or 300. Using the example above, if the user uses their hand 402a to move the first control member 204 back and forth along a line A (illustrated in FIG. 2C, FIG. 2D, and FIG. 4B), the movement command resulting from the control signal generated will cause the control target 410b to rotate a tool member or end effector 410c about a joint 410d along an arc AAA, illustrated in FIG. 4F. If the user uses their hand 402a to rotate the first control member 204 back and forth about its longitudinal axis about an arc B (illustrated in FIG. 2G and FIG. 4B), the movement command resulting from the control signal generated will cause the control target 410b to rotate the tool member or end effector 410c about a joint 410e along an arc BBB, illustrated in FIG. 4F. If the user uses his/her hand 402a to move the first control member 204 side to side along a line C (illustrated in FIG. 2E, FIG. 2F, and FIG. 4B), the movement command resulting from the control signal generated will cause the control target 410b to rotate the tool member or end effector 410c about a joint 410f along an arc CCC, illustrated in FIG. 4F.

Furthermore, if the user uses his/her thumb 402b to move the second control member 208 forwards and backwards along a line E (illustrated in FIG. 2E, FIG. 2F, FIG. 2G, and FIG. 4B), the movement command resulting from the control signal generated will cause the tool member or end effector 410c to move along a line EEE (i.e., its x-axis), illustrated in FIG. 4F. If the user uses his/her thumb 402b to move the second control member 208 back and forth along a line E (illustrated in FIG. 2C, FIG. 2D, FIG. 2G, and FIG. 4B), the movement command resulting from the control signal generated will cause the control target 410b to move along a line EEE (i.e., its y-axis through the joint 410f), illustrated in FIG. 4F. If the user uses his/her thumb 402b to move the second control member 208 side to side along a line D (illustrated in FIG. 2C, FIG. 2D, FIG. 2E, FIG. 2F, and FIG. 4B), the movement command resulting from the control signal generated will cause the tool member or end effector 410c to move along a line DDD (i.e., its z-axis), illustrated in FIG. 4F. In some embodiments, the control button 206 and/or other control buttons on the controller 102, 200, or 300 may be used to, for example, perform actions using the tool member 210c. Furthermore one of ordinary skill in the art will recognize that the tool member or end effector 410c illustrated in FIG. 4F may be replaced or supplemented with a variety of tool members (e.g., surgical instruments and the like) without departing from the scope of the present disclosure. As discussed above, the control target 410a may include a camera on or adjacent the tool member or end effector 410c to provide a field of view to allow navigation to a target.

Figure 5:
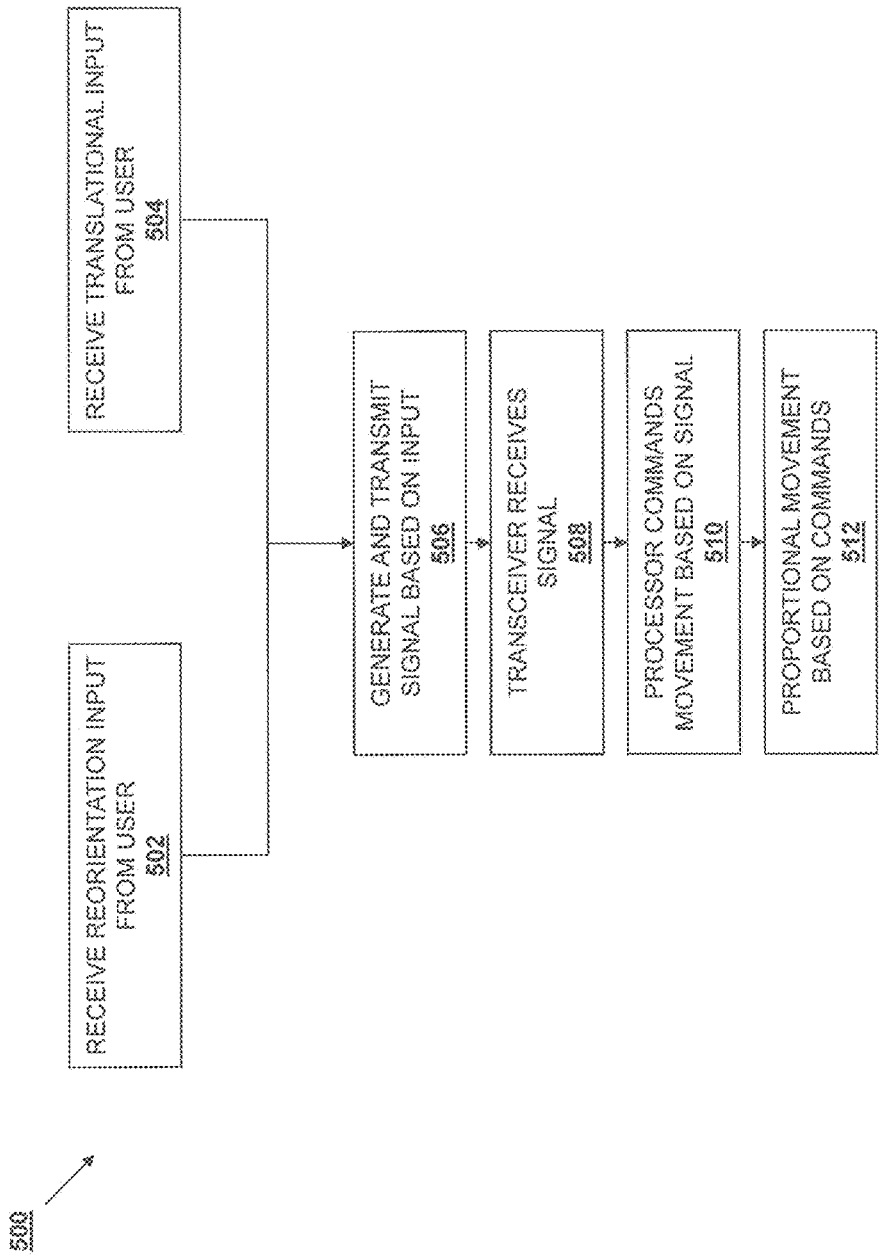
FIG. 5 is a flowchart illustrating an embodiment of a method for controlling a control target.

Referring now to FIG. 5, a method 500 for controlling a control target is illustrated. As is the case with the other methods described herein, various embodiments may not include all of the steps described below, may include additional steps, and may sequence the steps differently. Accordingly, the specific arrangement of steps shown in FIG. 5 should not be construed as limiting the scope of controlling the movement of a control target.

The method 500 may begin at block 502 where rotational input is received from a user. The user may provide rotational input by repositioning the first control member 204 of the controller 200 or 300 similarly as discussed above. In some embodiments, the rotational input may be manually detected by a physical device such as an actuator. In other embodiments, the rotational input may be electrically detected by a sensor such as an accelerometer.

The method 500 may proceed simultaneously with block 504 where translational input is received from the user. The user may provide translational input by repositioning the second control member 208 of the controller 200 or 300 similarly as discussed above. The rotational input and the translational input may be provided by the user simultaneously using a single hand of the user. In some embodiments, the translational input may be manually detected by a physical device such as an actuator.

In an embodiment, the rotational and translational input may be provided by a user viewing the current position of a control target 106 on a display screen. For example, the user may be viewing the current position of a surgical device presented within a virtual representation of a patient on a display screen. In this example, the rotational input and translational input may be provided using the current view on the display screen as a frame of reference.

The method 500 then proceeds to block 506 where a control signal is generated based on the rotational input and translational input and then transmitted. In the case of the rotational input being manually detected, the control signal may be generated based on the rotational input and translational input as detected by a number of actuators, which convert the mechanical force being asserted on the first control member 204 and the second control member 208 to an electrical signal to be interpreted as rotational input and translational input, respectively. In the case of the rotational input being electronically detected, the control signal may be generated based on rotational input as detected by accelerometers and translational input as detected by actuators.

In an embodiment, a control signal may be generated based on the rotational input and translational input according to the BLUETOOTH® protocol. Once generated, the control signal may be transmitted as an RF signal by an RF transmitter according to the BLUETOOTH® protocol. One of ordinary skill in the art will appreciate that an RF signal may be generated and transmitted according to a variety of other RF protocols such as the ZIGBEE® protocol, the Wireless USB protocol, etc. In other examples, the control signal may be transmitted as an IR signal, visible light signal, or as some other signal suitable for transmitting the control information.

The method 500 then proceeds to block 508, the transceiver 104a of the signal conversion system 104 receives the control signal. In the case that the control signal is an RF signal, the transceiver 104a includes an RF sensor configured to receive a signal according to the appropriate protocol (e.g., BLUETOOTH®, ZIGBEE®, Wireless USB, etc.). In other embodiments, the control signal may be transmitted over a wired connection. In this case, the transmitter 102f and the transceiver 104a are physically connected by a cable such as a universal serial bus (USB) cable, serial cable, parallel cable, proprietary cable, etc.

The method 500 then proceeds to block 510 where the conversion processor 104b commands movement in 6 DOF based on the received control signal. Specifically, the control signal may be converted to movement commands based on the rotational and/or translational input in the control signal. The movement commands may specify parameters for defining the movement of a point of view or a virtual representation of the user in one or more DOF in a virtual 3D environment. For example, if the second control member 208 is repositioned upward by the user, the resulting control signal may be used to generate a movement command for moving a point of view of a surgical device up along the z-axis within a 3D representation of a patient's body. In another example, if the first control member 204 is tilted to the left and the second control member 208 is repositioned downward, the resulting control signal may be used to generate movement commands for rolling a surgical device to the left while moving the surgical device down along a z-axis in the 3D representation of the patient's body. Any combination of rotational and translational input may be provided to generate movement commands with varying combinations of parameters in one or more DOF.

The method 500 then proceeds to block 512 where a proportional movement is performed in the virtual and/or real environment based on the movement commands. For example, a point of view of a surgical device in a virtual representation of a patient may be repositioned according to the movement commands, where the point of view corresponds to a camera or sensor affixed to a surgical device. In this example, the surgical device may also be repositioned in the patient's body according to the movement of the surgical device in the virtual representation of the patient's body. The unified controller allows the surgeon to navigate the surgical device in 6-DOF within the patient's body with a single hand.

Figure 6:
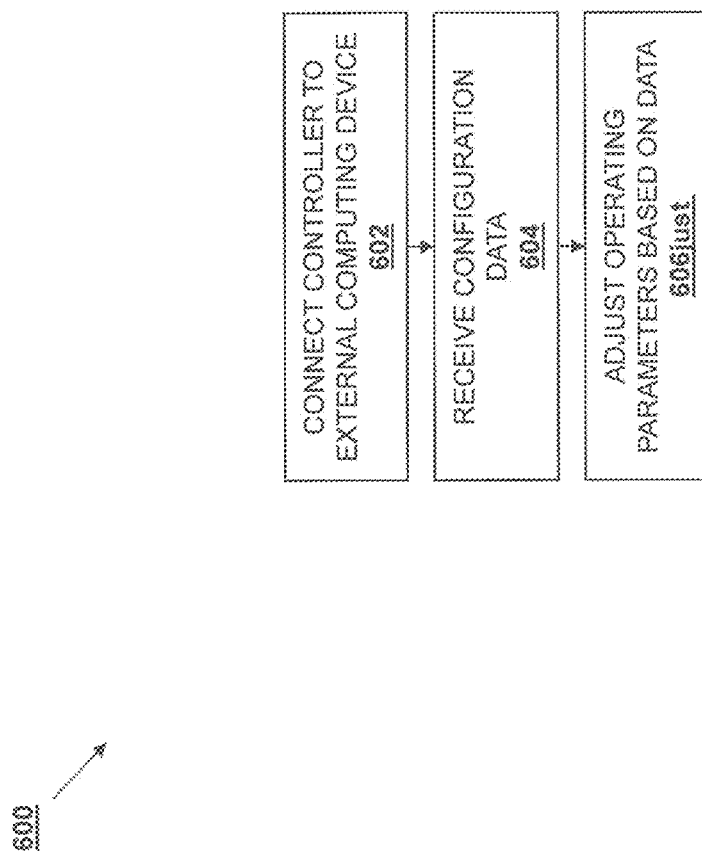
FIG. 6 is a flowchart illustrating an embodiment of a method for configuring a controller.

Referring now to FIG. 6, a method 600 for configuring a controller is illustrated. As is the case with the other methods described herein, various embodiments may not include all of the steps described below, may include additional steps, and may sequence the steps differently. Accordingly, the specific arrangement of steps shown in FIG. 6 should not be construed as limiting the scope of controlling the movement of a control target.

The method 600 begins at block 602 where the controller 102 is connected to an external computing device. The controller 102 may be connected via a physical connection (e.g., USB cable) or any number of wireless protocols (e.g., BLUETOOTH® protocol). The external computing device may be preconfigured with software for interfacing with the controller 102.

The method 600 then proceeds to block 604 where configuration data is received by the controller 102 from the external computing device. The configuration data may specify configuration parameters such as gains (i.e., sensitivity), rates of onset (i.e., lag), deadbands (i.e., neutral), and/or limits (i.e., maximum angular displacement). The configuration data may also assign movement commands for a control target to movements of the first control member and second control member. The configuration parameters may be specified by the user using the software configured to interface with the controller 102.

The method 600 then proceeds to block 606 where the operating parameters of the controller 102 are adjusted based on the configuration data. The operating parameters may be stored in memory and then used by the controller 102 to remotely control a control target as discussed above with respect to FIG. 4A and FIG. 5. In some embodiments, the method 600 may include the ability to set "trim", establish rates of translation (e.g., cm/sec) or reorientation (e.g., deg/sec), or initiate "auto-sequences" to auto-pilot movements (on a display or on the controller 102 itself.)

In other embodiments, the controller 102 may be equipped with an input device that allows the user to directly configure the operating parameters of the controller 102. For example, the controller 102 may include a display screen with configuration menus that are navigable using the first control member 204 and/or the second control member 208.

A computer readable program product stored on a tangible storage media may be used to facilitate any of the preceding embodiments such as, for example, the control program discussed above. For example, embodiments of the invention may be stored on a computer readable medium such as an optical disk [e.g., compact disc (CD), digital versatile disc (DVD), etc.], a diskette, a tape, a file, a flash memory card, or any other computer readable storage device. In this example, the execution of the computer readable program product may cause a processor to perform the methods discussed above with respect to FIG. 4A, FIG. 5, and FIG. 6.

Figure 7A:
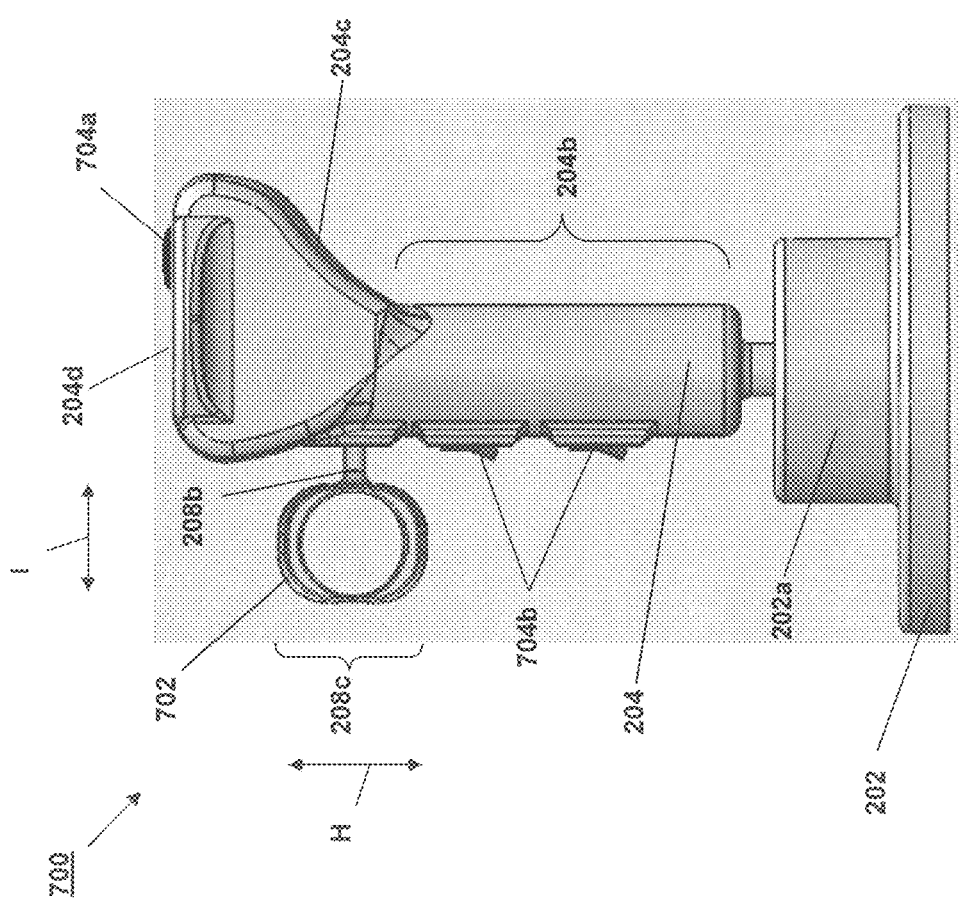
FIG. 7A is a side view illustrating an embodiment of a controller.

Referring now to FIG. 7A and FIG. 7B, a controller 700 is illustrated that is substantially similar in structure and operation to the controller 200, discussed above with reference to FIG. 2A, FIG. 2B, FIG. 2C, FIG. 2D, FIG. 2E, FIG. 2F, FIG. 2G, FIG. 4A, FIG. 4B, FIG. 4C, FIG. 4D, FIG. 4E, FIG. 4F, FIG. 5, and FIG. 6, with the provision of a second control member 702 replacing the second control member 208, and a plurality of control buttons 704a and 704b in place of the control button 206. The second control member 702 is substantially similar in structure and operation to the second control member 208, but is positioned on a front surface of the controller 102 at the junction of the first section 204b and the grip portion 204c of the first control member 204. The control button 704a is located on the top surface 204d of the grip portion 204c of the first control member 204, while the control buttons 704b are located on the front surface of the controller 102 below the second control member 702.

In operation, the first control member 204 may operate substantially as described above according to the methods 400 and 500. However, inputs provided using the second control member 702 be configured to provide different control signals. For example, the user may use the index finger 402c (illustrated in FIG. 4B) to move the second control member 702 side to side along a line G (e.g., on its coupling to the first control member 204), in order to provide y-axis inputs to the controller 700. Furthermore, the user may use the index finger 402c to move the second control member 702 up and down along a line H (e.g., on its coupling to the first control member 204), in order to provide z-axis inputs to the controller 700. Further still, the user may use the finger 402c to move the second control member 702 forward and backward along a line I (e.g., on its coupling to the first control member 204 including, in some embodiments, with resistance from a resilient member similar to the resilient member 209), in order to provide x-axis inputs to the controller 700. In an embodiment, the resilient member may provide a neutral position of the second control member 702 such that compressing the resilient member using the second control member 702 provides a first y-axis input for y-axis movement of the control target 106 in a first direction, and extending the resilient member using the second control member 702 provides a second y-axis input for y-axis movement of the control target 106 in a second direction that is opposite the first direction. Furthermore, the control buttons 704a and 704b may be actuated to control a variety of other systems on the control target, as discussed above.

Figure 8B:
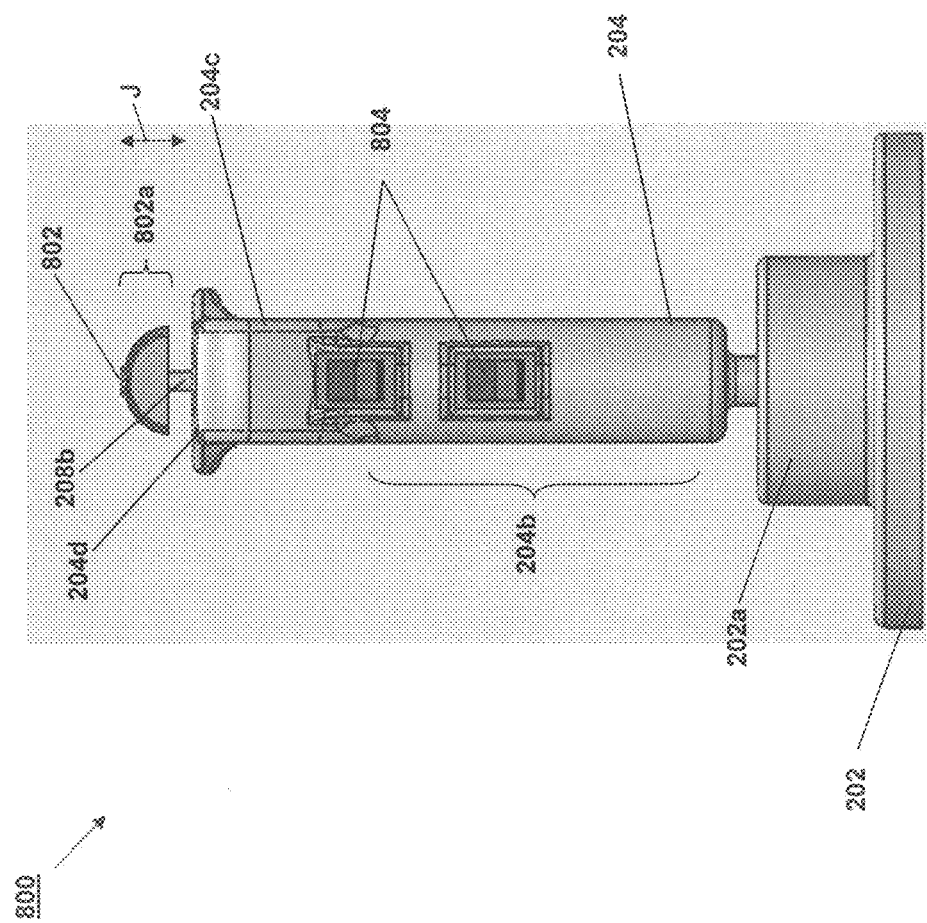
FIG. 8B is a front view illustrating an embodiment of the controller of FIG. 8A.

Referring now to FIG. 8A and FIG. 8B, a controller 800 is illustrated that is substantially similar in structure and operation to the controller 200, discussed above with reference to FIG. 2A, FIG. 2B, FIG. 2C, FIG. 2D, FIG. 2E, FIG. 2F, FIG. 2G, FIG. 4A, FIG. 4B, FIG. 4C, FIG. 4D, FIG. 4E, FIG. 4F, FIG. 5, and FIG. 6, with the provision of a second control member 802 replacing the second control member 208, and a plurality of control buttons 804 in place of the control button 206. The second control member 802 is similar in structure and operation to the second control member 208, but includes an actuation portion 802a replacing the actuation portion 208c. As can be seen, the actuation portion 802a does not include the thumb channel defined by the actuation portion 208c. The control buttons 804 are located on the front surface of the controller 102.

In operation, the first control member 204 may operate substantially as described above according to the methods 400 and 500. The second control member 802 may operate substantially as described above for the second control member 208 according to the methods 400 and 500, but with some modifications. For example, some inputs provided using the second control member 802 be configured to provide different control signals. For example, the user may use the thumb 402c to move the second control member 802 up and down along a line J (e.g., on its coupling to the first control member 204) by compressing the resilient member 209 in order to provide z-axis inputs to the controller 800. In some embodiments, compressing the resilient member 209 initially may provide a first z-axis input for z-axis movement of the control target 106 in a first direction, while a release of the second control member 802 and then a recompression of the resilient member 209 using the second control member 802 may provide a second z-axis input for z-axis movement of the control target 106 in a second direction that is opposite the first direction. In other embodiments, one of the control buttons 804 may determine which z-axis direction compressing the second control member 802 will provide (e.g., with a control button 804 in a first position, compressing the second control member 802 will provide a z-axis input for z-axis movement of the control target in a first direction, while with that control button 804 in a second position, compressing the second control member 802 will provide a z-axis input for z-axis movement of the control target in a second direction that is opposite the first direction.) Furthermore, the control buttons 804 may be actuated to control a variety of other systems on the control target, as discussed above.

Referring now to FIG. 9A and FIG. 9B, a controller 900 is illustrated that is substantially similar in structure and operation to the controller 200, discussed above with reference to FIG. 2A, FIG. 2Bb, FIG. 2C, FIG. 2D, FIG. 2E, FIG. 2F, FIG. 2G, FIG. 4A, FIG. 4B, FIG. 4C, FIG. 4D, FIG. 4E, FIG. 4F, FIG. 5, and FIG. 6, with the provision of a second control member 902 replacing the second control member 208. The second control member 902 is a compressible button having first direction actuation portions 902a, second direction actuation portions 902b, and third direction actuation portion 902c.

In operation, the first control member 204 may operate substantially as described above according to the methods 400 and 500. The second control member 802 may operate substantially as described above for the second control member 208 according to the methods 400 and 500, but with some modifications. For example, the user may use the thumb 402b to press the actuation portions 902a on the second control member 902 in order to provide x-axis inputs to the controller 900. Furthermore, the user may use the thumb 402b to press the actuation portions 902b on the second control member 902 in order to provide y-axis inputs to the controller 900. Further still, the user may use the thumb 402b to press the actuation portion 902c on the second control member 902 in order to provide z-axis inputs to the controller 900. In an embodiment, pressing the actuation portion 902c on the second control member 902 may provide a first z-axis input for z-axis movement of the control target 106 in a first direction, while releasing and then re-pressing the actuation portion 902c on the second control member 702 may provide a second z-axis input for z-axis movement of the control target 106 in a second direction that is opposite the first direction. In other embodiments, the control button 206 may determine which z-axis direction pressing the actuation portion 902c on the second control member 902 will provide (e.g., with a control button 206 in a first position, pressing the actuation portion 902c on the second control member 902 will provide a z-axis input for z-axis movement of the control target in a first direction, while with that control button 804 in a second position, pressing the actuation portion 902c on the second control member 902 will provide a z-axis input for z-axis movement of the control target in a second direction that is opposite the first direction.)

Thus, a system and method have been described that that include a controller that allows a user to provide rotational and translational commands in six independent degrees of freedom using a single hand. The system and method may be utilized in a wide variety of control scenarios. While a number of control scenarios are discussed below, those examples are not meant to be limiting, and one of ordinary skill in the art will recognize that any control scenario may benefit from being able to provide rotational and translational movement using a single hand.

In an embodiment, the control systems and methods discussed above may be utilized in a wide variety of medical applications. While a number of medical applications are discussed below, those examples are not meant to be limiting, and one of ordinary skill in the art will recognize that many other medical applications may benefit from being able to provide rotational and translational movement using a single hand. Furthermore, in such embodiments, in addition to the rotational and translational movement provided using first and second control members discussed above, control buttons (e.g., the control button 206 on controllers 200 or 300 and/or other control buttons) may be configured for tasks such as, for example, end-effector capture, biopsy, suturing, radiography, photography, and/or a variety of other medical tasks as may be known by one or more of ordinary skill in the art.

For example, the control systems and methods discussed above may provide a control system for performing laparoscopic surgery and/or a method for performing laparoscopic surgery. Conventional laparoscopic surgery is performed using control systems that require both hands of a surgeon to operate the control system. Using the control systems and/or the methods discussed above provide several benefits in performing laparoscopic surgery, including fine dexterous manipulation of one or more surgical instruments, potentially without a straight and rigid path to the end effector.

In another example, the control systems and methods discussed above may provide a control system for performing minimally invasive or natural orifice surgery and/or a method for performing minimally-invasive or natural-orifice surgery. Conventional minimally invasive or natural orifice surgery is performed using control systems that require both hands of a surgeon to operate the control system. Using the control systems and/or the methods discussed above provide several benefits in performing minimally invasive or natural orifice surgery, including fine dexterous manipulation of one or more surgical tools, potentially without a straight and rigid path to the end effector.

In another example, the control systems and methods discussed above may provide a control system for performing prenatal intrauterine surgery and/or a method for performing prenatal surgery. Conventional prenatal surgery is performed using control systems that require both hands of a surgeon to operate the control system in very tight confines. Using the control systems and/or the methods discussed above provide several benefits in performing prenatal surgery, including fine dexterous manipulation of one or more surgical tools, potentially without a straight and rigid path to the end effector.

For any of the above surgical examples, the control systems and methods discussed above may provide a very stable control system for performing microscopic surgery and/or a method for performing microscopic surgery. Using the control systems and/or the methods discussed above provide several benefits in performing microscopic surgery, including highly accurate camera and end effector pointing.

In another example, the control systems and methods discussed above may provide a control system for performing interventional radiology and/or a method for performing interventional radiology. Conventional interventional radiology is performed using control systems that require both hands of a surgeon to operate the control system. Using the control systems and/or the methods discussed above provide several benefits in performing interventional radiology, including highly accurate navigation through for interventional radiology.

In another example, the control systems and methods discussed above may provide a control system for performing interventional cardiology and/or a method for performing interventional cardiology. Conventional interventional cardiology is performed using control systems that require both hands of an interventionist to operate the control system. Using the control systems and/or the methods discussed above provide several benefits in performing interventional cardiology, including highly accurate navigation through the vascular tree using one hand.

In another example, the control systems and methods discussed above may provide a control system including Hansen/Da Vinci robotic control and/or a method for performing Hansen/Da Vinci robotic control. Conventional Hansen/Da Vinci robotic control is performed using control systems that require both hands of a surgeon to operate the control system. Using the control systems and/or the methods discussed above provide several benefits in performing Hansen/Da Vinci robotic control, including fluid, continuous translation and reorientation without shuffling the end effector for longer motions.

In another example, the control systems and methods discussed above may provide a control system for performing 3D- or 4D-image guidance and/or a method for performing 3D- or 4D-image guidance. Conventional 3D- or 4D-image guidance is performed using control systems that require both hands of a surgeon to operate the control system. Using the control systems and/or the methods discussed above provide several benefits in performing 3D- or 4D-image guidance, including fluid, continuous translation and reorientation without shuffling the end effector for longer motions.

In another example, the control systems and methods discussed above may provide a control system for performing endoscopy and/or a method for performing endoscopy. Conventional endoscopy is performed using control systems that require both hands of a surgeon to operate the control system. Using the control systems and/or the methods discussed above provide several benefits in performing endoscopy, including fluid, continuous translation and reorientation without shuffling the end effector for longer motions. This also applies to colonoscopy, cystoscopy, bronchoscopy, and other flexible inspection scopes.

In an embodiment, the control systems and methods discussed above may be utilized in a wide variety of defense or military applications. While a number of defense or military applications are discussed below, those examples are not meant to be limiting, and one of ordinary skill in the art will recognize that many other defense or military applications may benefit from being able to provide rotational and translational movement using a single hand.

For example, the control systems and methods discussed above may provide a control system for unmanned aerial systems and/or a method for controlling unmanned aerial systems. Conventional unmanned aerial systems are controlled using control systems that require both hands of an operator to operate the control system. Using the control systems and/or the methods discussed above provide several benefits in controlling unmanned aerial systems, including intuitive single-handed, precise, non-cross-coupled motion within the airspace.

In another example, the control systems and methods discussed above may provide a control system for unmanned submersible systems and/or a method for controlling unmanned submersible systems. Conventional unmanned submersible systems are controlled using control systems that require both hands of an operator to operate the control system. Using the control systems and/or the methods discussed above provide several benefits in controlling unmanned submersible systems, including intuitive single-handed, precise, non-cross-coupled motion within the submersible space.

In another example, the control systems and methods discussed above may provide a control system for weapons targeting systems and/or a method for controlling weapons targeting systems. Conventional weapons targeting systems are controlled using control systems that require both hands of an operator to operate the control system. Using the control systems and/or the methods discussed above provide several benefits in controlling weapons targeting systems, including precise, intuitive, single-handed targeting.

In another example, the control systems and methods discussed above may provide a control system for counter-improvised-explosive-device (TED) systems and/or a method for controlling counter-IED systems. Conventional counter-IED systems are controlled using control systems that require both hands of an operator to operate the control system. Using the control systems and/or the methods discussed above provide several benefits in controlling counter-IED systems, including precise, intuitive, single-handed pointing or targeting.

In another example, the control systems and methods discussed above may provide a control system for heavy mechanized vehicles and/or a method for controlling heavy mechanized vehicles. Conventional heavy mechanized vehicles are controlled using control systems that require both hands of an operator to operate the control system. Using the control systems and/or the methods discussed above provide several benefits in controlling heavy mechanized vehicles, including precise, intuitive, single-handed targeting.

In another example, the control systems and methods discussed above may provide a control system for piloted aircraft (e.g., rotary wing aircraft) and/or a method for controlling piloted aircraft. Conventional piloted aircraft are controlled using control systems that require both hands of an operator to operate the control system. Using the control systems and/or the methods discussed above provide several benefits in controlling piloted aircraft, including precise, intuitive, single-handed, non-cross-coupled motion within the airspace for the piloted aircraft.

In another example, the control systems and methods discussed above may provide a control system for spacecraft rendezvous and docking and/or a method for controlling spacecraft rendezvous and docking. Conventional spacecraft rendezvous and docking is controlled using control systems that require both hands of an operator to operate the control system. Using the control systems and/or the methods discussed above provide several benefits in controlling spacecraft rendezvous and docking, including precise, intuitive, single-handed, non-cross-coupled motion within the space for rendezvous and/or docking.

In another example, the control systems and methods discussed above may provide a control system for air-to-air refueling (e.g., boom control) and/or a method for controlling air-to-air refueling. Conventional air-to-air refueling is controlled using control systems that require both hands of an operator to operate the control system. Using the control systems and/or the methods discussed above provide several benefits in controlling air-to-air refueling, including precise, intuitive, single-handed, non-cross-coupled motion within the airspace for refueling.

In another example, the control systems and methods discussed above may provide a control system for navigation in virtual environments (e.g., operational and simulated warfare) and/or a method for controlling navigation in virtual environments. Conventional navigation in virtual environments is controlled using control systems that require both hands of an operator to operate the control system. Using the control systems and/or the methods discussed above provide several benefits in controlling navigation in virtual environments, including precise, intuitive, single-handed, non-cross-coupled motion within the virtual environment.

In an embodiment, the control systems and methods discussed above may be utilized in a wide variety of industrial applications. While a number of industrial applications are discussed below, those examples are not meant to be limiting, and one of ordinary skill in the art will recognize that many other industrial applications may benefit from being able to provide rotational and translational movement using a single hand.

For example, the control systems and methods discussed above may provide a control system for oil exploration systems (e.g., drills, 3D visualization tools, etc.) and/or a method for controlling oil exploration systems. Conventional oil exploration systems are controlled using control systems that require both hands of an operator to operate the control system. Using the control systems and/or the methods discussed above provide several benefits in controlling oil exploration systems, including precise, intuitive, single-handed, non-cross-coupled motion within the formation.

In another example, the control systems and methods discussed above may provide a control system for overhead cranes and/or a method for controlling overhead cranes. Conventional overhead cranes are controlled using control systems that require both hands of an operator to operate the control system. Using the control systems and/or the methods discussed above provide a benefit in controlling overhead cranes where single axis motion is often limited, by speeding up the process and increasing accuracy.

In another example, the control systems and methods discussed above may provide a control system for cherry pickers or other mobile industrial lifts and/or a method for controlling cherry pickers or other mobile industrial lifts. Conventional cherry pickers or other mobile industrial lifts are often controlled using control systems that require both hands of an operator to operate the control system, and often allow translation (i.e., x, y, and/or z motion) in only one direction at a time. Using the control systems and/or the methods discussed above provide several benefits in controlling cherry pickers or other mobile industrial lifts, including simultaneous multi-axis motion via a single-handed controller.

In another example, the control systems and methods discussed above may provide a control system for firefighting systems (e.g., water cannons, ladder trucks, etc.) and/or a method for controlling firefighting systems. Conventional firefighting systems are often controlled using control systems that require both hands of an operator to operate the control system, and typically do not allow multi-axis reorientation and translation. Using the control systems and/or the methods discussed above provide several benefits in controlling firefighting systems, including simultaneous multi-axis motion via a single-handed controller.

In another example, the control systems and methods discussed above may provide a control system for nuclear material handling (e.g., gloveboxes, fuel rods in cores, etc.) and/or a method for controlling nuclear material handling. Conventional nuclear material handling systems are controlled using control systems that require both hands of an operator to operate the control system. Using the control systems and/or the methods discussed above provide several benefits in controlling nuclear material handling, including very precise, fluid, single-handed, multi-axis operations with sensitive materials.

In another example, the control systems and methods discussed above may provide a control system for steel manufacturing and other high temperature processes and/or a method for controlling steel manufacturing and other high temperature processes. Conventional steel manufacturing and other high temperature processes are controlled using control systems that require both hands of an operator to operate the control system. Using the control systems and/or the methods discussed above provide several benefits in controlling steel manufacturing and other high temperature processes, including very precise, fluid, single-handed, multi-axis operations with sensitive materials.

In another example, the control systems and methods discussed above may provide a control system for explosives handling (e.g., in mining applications) and/or a method for controlling explosives handling. Conventional explosives handling is controlled using control systems that require both hands of an operator to operate the control system. Using the control systems and/or the methods discussed above provide several benefits in controlling explosives handling, including very precise, fluid, single-handed, multi-axis operations with sensitive materials.

In another example, the control systems and methods discussed above may provide a control system for waste management systems and/or a method for controlling waste management systems. Conventional waste management systems are controlled using control systems that require both hands of an operator to operate the control system. Using the control systems and/or the methods discussed above provide several benefits in controlling waste management systems, including very precise, fluid, single-handed, multi-axis operations with sensitive materials.

In an embodiment, the control systems and methods discussed above may be utilized in a wide variety of consumer applications. While a number of consumer applications are discussed below, those examples are not meant to be limiting, and one of ordinary skill in the art will recognize that many other consumer applications may benefit from being able to provide rotational and translational movement using a single hand.

For example, the control systems and methods discussed above may provide a control system for consumer electronics devices [e.g., Nintendo WHO (Nintendo of America Inc., Redmond, Wash., USA), Nintendo DS®, Microsoft XBox® (Microsoft Corp., Redmond, Wash., USA), Sony Playstation® (Sony Computer Entertainment Inc., Corp., Tokyo, Japan)], and other video consoles as may be known by one or more of ordinary skill in the art) and/or a method for controlling consumer electronics devices. Conventional consumer electronics devices are controlled using control systems that require both hands of an operator to operate the control system (e.g., a hand controller and keyboard, two hands on one controller, a Wii® "nunchuck" z-handed I/O device, etc.) Using the control systems and/or the methods discussed above provide several benefits in controlling consumer electronics devices, including the ability to navigate with precision through virtual space with fluidity, precision and speed via an intuitive, single-handed controller.

In another example, the control systems and methods discussed above may provide a control system for computer navigation in 3D and/or a method for controlling computer navigation in 3D. Conventional computer navigation in 3D is controlled using control systems that either require both hands of an operator to operate the control system or do not allow fluid multi-axis motion through space. Using the control systems and/or the methods discussed above provide several benefits in controlling computer navigation in 3D, including very precise, fluid, single-handed, multi-axis operations.

In another example, the control systems and methods discussed above may provide a control system for radio-controlled vehicles and/or a method for controlling radio-controlled vehicles. Conventional radio-controlled vehicles are controlled using control systems that require both hands of an operator to operate the control system. Using the control systems and/or the methods discussed above provide several benefits in controlling radio-controlled vehicles, including intuitive single-handed, precise, non-cross-coupled motion within the airspace for radio-controlled vehicles.

In another example, the control systems and methods discussed above may provide a control system for 3D computer aided drafting (CAD) image manipulation and/or a method for controlling 3D CAD image manipulation. Conventional 3D CAD image manipulation is controlled using control systems that either require both hands of an operator to operate the control system or do not allow fluid multi-axis motion through 3D space. Using the control systems and/or the methods discussed above provide several benefits in controlling 3D CAD image manipulation, including intuitive single-handed, precise, non-cross-coupled motion within the 3D space.

In another example, the control systems and methods discussed above may provide a control system for general aviation and/or a method for controlling general aviation. Conventional general aviation is controlled using control systems that require both hands and feet of an operator to operate the control system. Using the control systems and/or the methods discussed above provide several benefits in controlling general aviation, including intuitive single-handed, precise, non-cross-coupled motion within the airspace for general aviation.

It is understood that variations may be made in the above without departing from the scope of the invention. While specific embodiments have been shown and described, modifications can be made by one skilled in the art without departing from the spirit or teaching of this invention. The embodiments as described are exemplary only and are not limiting. Many variations and modifications are possible and are within the scope of the invention. Furthermore, one or more elements of the exemplary embodiments may be omitted, combined with, or substituted for, in whole or in part, with one or more elements of one or more of the other exemplary embodiments. Accordingly, the scope of protection is not limited to the embodiments described, but is only limited by the claims that follow, the scope of which shall include all equivalents of the subject matter of the claims.

What is claimed is:

1. A controller, comprising:
a unified hand controller including:
a first control member configured to be grasped by a user's hand, wherein the first control member is movable back and forth through three continuous and independent degrees freedom to provide in response thereto a corresponding first set of three independent control inputs; and
a second control member extending from the first control member and configured to engaged by one of the thumb or the index finger of the user's hand, wherein the second control member is movable independently of the first control member back and forth through three continuous and independent degrees of freedom to provide in response thereto a corresponding second set of three independent control inputs, the first set of control inputs being independent of the second set of control inputs, wherein the second control member includes a channel for the insertion of said one of the thumb or the index finger of the user's hand whereby the second control member is movable through the three continuous and independent degrees of freedom thereof; and
a controller processor connectable to receive the first and second set of control inputs and generate therefrom a respective first and second set of control signals, wherein the first set of control signals corresponds to three independent rotational movements of a control target and are proportional to a displacement of the first control member through the corresponding first set of degrees of freedom, and wherein the second set of control signals corresponds to three independent translational movements of the control target and are proportional to the displacement of the second control member through the corresponding second set of degrees of freedom.

2. The controller of claim 1, further comprising:
a transmitter connectable to the controller processor to receive the first and second set of control signals and transmit the first and second set of control signals to the control target.

3. The controller of claim 2, wherein the transmitter is configured to transmit the control signals through a wired connection.

4. The controller of claim 2, wherein the transmitter is configured to transmit the control signals through a wire-less connection.

5. The controller of claim 1, wherein the control target is an aircraft.

6. The controller of claim 1, wherein the control target is a medical instrument.

7. The controller of claim 1, wherein the control target is in a virtual environment.

8. The controller of claim 1, wherein the unified hand controller further includes a discrete control element to provide a discrete control input.

9. The controller of claim 8, wherein the discrete control element is a control button formed on the first control member that is configured to be operated by one or more digits of the user's hand.

10. The controller of claim 9, wherein the discrete control input is an ON/OFF value.

11. The controller of claim 9, wherein the discrete control input is a trim function.

12. The controller of claim 1, wherein the first control member is moveably coupled to a base and is operable to produce the first set of control inputs in response to movement of the first control member relative to the base.

13. The controller of claim 1, wherein the first control member comprises at least one motion sensor and is operable to produce the first set of control inputs in response to movement of the first control member in space that is detected by the at least one motion sensor.

14. The controller of claim 1, wherein the control target is a medical-surgical device.

15. A control system, comprising:
a controller, including:
a unified hand controller including:
a first control member configured to be grasped by a user's hand, wherein the first control member is movable back and forth through three continuous and independent degrees freedom to provide in response thereto a corresponding first set of three independent control inputs; and
a second control member extending from the first control member and configured to engaged by one of the thumb or the index finger of the user's hand, wherein the second control member is movable independently of the first control member back and forth through three continuous and independent degrees of freedom to provide in response thereto a corresponding second set of three independent control inputs, the first set of control inputs being independent of the second set of control inputs, wherein the second control member includes a channel for the insertion of said one of the thumb or the index finger of the user's hand whereby the second control member is movable through the three continuous and independent degrees of freedom thereof; and
a controller processor connectable to receive the first and second set of control inputs and generate therefrom a respective first and second set of control signals; and a control target connectable to receive the first and second sets of control signals, the control target including a tool having a member, the member having three independent and continuous rotational movements corresponding the first set of control signals that are proportional to a displacement of the first control member along the corresponding first set of degrees of freedom, and having three independent and continuous translational movements corresponding the second set of control signals that are proportional to the displacement of the second control member along the corresponding second set of degrees of freedom.

16. The control system of claim 15, further comprising:
a transmitter connectable to the controller processor to receive the first and second set of control signals and transmit the first and second set of control signals to the control target.

17. The control system of claim 16, wherein the transmitter is configured to transmit the control signals through a wired connection.

18. The control system of claim 16, wherein the transmitter is configured to transmit the control signals through a wire-less connection.

19. The control system of claim 15, wherein the tool is a medical-surgical device.

20. The control system of claim 15, wherein the tool is a medical instrument.

21. The control system of claim 15, wherein the unified hand controller further includes a discrete control element to provide a discrete control input.

22. The control system of claim 21, wherein the discrete control element is a control button formed on the first control member that is configured to be operated by one or more digits of the user's hand.

23. The control system of claim 22, wherein the discrete control input is an ON/OFF value.

24. The control system of claim 22, wherein the discrete control input is a trim function.

25. The control system of claim 15, wherein the first control member is moveably coupled to a base and is operable to produce the first set of control inputs in response to movement of the first control member relative to the base.

26. The control system of claim 15, wherein the first control member comprises at least one motion sensor and is operable to produce the first set of control inputs in response to movement of the first control member in space that is detected by the at least one motion sensor.

27. The control system of claim 15, wherein the tool is an industrial device.

\* \* \* \* \*